United States Patent
Herrera Sanchez et al.

(10) Patent No.: US 10,357,519 B2
(45) Date of Patent: Jul. 23, 2019

(54) CONDITIONED MEDIUM OF LIVER PROGENITOR CELLS

(71) Applicant: Fresenius Medical Care Deutschland GmbH, Bad Homburg (DE)

(72) Inventors: Maria Beatriz Herrera Sanchez, Turin (IT); Valentina Fonsato, Cambiano (IT); Ciro Tetta, Mirandola (IT); Giovanni Camussi, Turin (IT)

(73) Assignee: FRESENIUS MEDICAL CARE DEUTSCHLAND GMBH, Bad Homburg (DE)

(*) Notice: Subject to any disclaimer, the term of this patent is extended or adjusted under 35 U.S.C. 154(b) by 31 days.

(21) Appl. No.: 15/412,142

(22) Filed: Jan. 23, 2017

(65) Prior Publication Data

US 2017/0182100 A1    Jun. 29, 2017

Related U.S. Application Data

(62) Division of application No. 12/737,143, filed as application No. PCT/EP2009/057232 on Jun. 11, 2009.

(30) Foreign Application Priority Data

Jun. 11, 2008 (EP) .................................. 08010651

(51) Int. Cl.

| | | |
|---|---|---|
| *A61K 35/407* | (2015.01) | |
| *A61K 38/17* | (2006.01) | |
| *A61K 38/18* | (2006.01) | |
| *A61K 38/20* | (2006.01) | |
| *A61K 38/30* | (2006.01) | |
| *C12N 5/071* | (2010.01) | |
| *C12N 5/00* | (2006.01) | |

(52) U.S. Cl.
CPC ........ *A61K 35/407* (2013.01); *A61K 38/1703* (2013.01); *A61K 38/1793* (2013.01); *A61K 38/1833* (2013.01); *A61K 38/1858* (2013.01); *A61K 38/1866* (2013.01); *A61K 38/204* (2013.01); *A61K 38/2053* (2013.01); *A61K 38/30* (2013.01); *C12N 5/0018* (2013.01); *C12N 5/067* (2013.01); *C12N 5/0672* (2013.01); *C12N 2500/05* (2013.01); *C12N 2500/32* (2013.01); *C12N 2500/38* (2013.01); *C12N 2500/84* (2013.01); *C12N 2501/11* (2013.01); *C12N 2501/115* (2013.01); *C12N 2501/998* (2013.01)

(58) Field of Classification Search
CPC .............. A61K 38/18; A61K 38/1833; A61K 38/1866; A61K 38/19; A61K 38/204; A61K 38/2053

See application file for complete search history.

(56) References Cited

U.S. PATENT DOCUMENTS

| | | |
|---|---|---|
| 6,475,490 B1 | 11/2002 | Srivastava et al. |
| 6,719,696 B2 | 4/2004 | Stergiopoulos et al. |
| 6,916,770 B2 | 7/2005 | Nitzsche |
| 2003/0054973 A1 | 3/2003 | Anversa |
| 2003/0138951 A1 | 7/2003 | Yin |
| 2004/0142861 A1 | 7/2004 | Mansbridge |
| 2007/0292400 A1* | 12/2007 | Lipton ............... A61K 8/982 424/93.7 |
| 2008/0206211 A1* | 8/2008 | Gueniche ........... A61K 8/981 424/93.42 |

FOREIGN PATENT DOCUMENTS

| | | |
|---|---|---|
| WO | WO 00/69449 | 11/2000 |
| WO | WO 2006/126219 | 11/2003 |
| WO | WO 2006/126236 | 11/2006 |

OTHER PUBLICATIONS

Banas et al. IFATS Collection: In vivo therapeutic potential of human adipose tissue mesenchymal stem cells after transplantation into mice with liver injury, Stem Cells, vol. 26, No. 10, pp. 2705-2712 Jun. 2008 (XP009121048).

Van Poll et al. Mesenchymal stem cell-derived molecules directly modulate hepatocellular death and regeneration in vitro and in vivo. Hepatology, vol. 47, No. 5, pp. 1634-1643. Jan. 2008.

Parekkadan et al. Mesenchymal stem cell derived molecules reverse fulminant hepatic failure. PLOS One, vol. 2, No. 9, e941, Sep. 2007.

Kobayashi et al. Cell choice for bioartificial livers. The Keio Journal of Medicine, vol. 52, No. 3, pp. 151-157, Sep. 2003.

Lehmann et al. Lethal toxicity of lipopolysaccharide and tumor necrosis factor in normal and D-Galactosmine-treated mice. J. Exp. Med., vol. 165, No. 3, pp. 657-663, Mar. 1987.

* cited by examiner

*Primary Examiner* — Ruth A Davis
(74) *Attorney, Agent, or Firm* — Jacobson Holman, PLLC.

(57) ABSTRACT

The invention is in the field of regenerative medicine. It has been found that the conditioned medium of non-oval pluripotent liver progenitor cells exerts a tissue regenerating effect. A preparation of the cell free conditioned medium is therefore useful in the treatment of injury and organ failure, preferably liver and/or injury or failure.

3 Claims, 13 Drawing Sheets

CONDITIONED MEDIUM OF LIVER PROGENITOR CELLS

The present invention is in the field of biological pharmaceutical preparations and regenerative medicine.

Stem cell preparations were shown to exert a regenerative effect on human or animal tissues. Clinical trials testing the efficacy of bioartificial liver support in treating fulminant hepatic failure (FHF) have provided some promising results, yet the current generation of devices has not demonstrated sufficient efficacy and reliability for routine use, primarily due to the lack of a functionally stable, human hepatocyte source (Kobayashi N, Okitsu T, Tanaka N. Cell choice for bioartificial livers. Keio J Med. 2003; 52(3):151-7.). Liver stem cells, or even stem cells derived from other tissues, could potentially provide an alternative source of human hepatocytes. In addition to bone marrow, stem cells reside in adult tissues such as the liver and the central nervous system, and have much greater plasticity than previously known.

The human liver pluripotent progenitor/stem cells described in International patent application WO2006/126236 were shown to undergo differentiation into a variety of tissue cell types and to exert organ regenerating effects. These cells are derived from a non-oval human liver pluripotent progenitor cell line which expresses hepatic cell markers.

International patent application WO2006/126236 also discloses a method of isolating the above-mentioned human liver pluripotent progenitor/stem cells capable of undergoing differentiation into a variety of cell types, the method comprising the steps of:
 (i) culturing adult liver-derived human mature hepatocytes in a cell culture medium until death of mature hepatocytes and selection of a population of surviving cells having epithelioid morphology;
 (ii) expanding the population of surviving cells having epithelioid morphology by culturing in a serum-containing, glucose-containing culture medium supplemented with hEGF (human epithelial growth factor) and bFGF (basic fibroblast growth factor) and comprising the usual inorganic salts, amino acids and vitamins necessary for the growth of mammalian cells and in particular wherein the mature hepatocytes are frozen in a serum-containing culture medium in the presence of a cryoprotecting agent and then thawed prior to culturing according to step (i).

The human pluripotent progenitor cells of WO2006/126236 (designated as HLSCs in the patent description) and the method of preparing thereof are herein fully incorporated by reference.

Preparations of mesenchymal stem cells (MSCs) were shown to exert a regenerative effect on tissue. For example, bone marrow-derived mesenchymal stem cells are known to naturally support hematopoiesis by secreting a number of trophic molecules, including soluble extracellular matrix glycoproteins, cytokines and growth factors.

However, stem cell preparations have the major disadvantage of causing immune reactions when administered. Some stem cell preparations even have the potential to cause cancer.

Parekkadan et al. (Parekkadan B, van Poll D, Suganuma K, Carter E A, Berthiaume F, Tilles A W, Yarmush M L. Mesenchymal stem cell-derived molecules reverse fulminant hepatic failure. PLoS ONE. 2007 Sep. 26; 2(9):e941) first assessed various MSC-treatments, such as delivery of conditioned medium (CM), to test their efficacy in a rat model of induced severe liver damage. In this paper, rats were intraperitoneally administered a total of two injections of D-galactosamine (Gal-N). In a second study (Van Poll D, Parekkadan B, Cho C H, Berthiaume F, Nahmias Y, Tilles A W, Yarmush M L. Mesenchymal stem cell-derived molecules directly modulate hepatocellular death and regeneration in vitro and in vivo. Hepatology. 2008 Jan. 24; 47(5): 1634-1643.) the Parekkadan's group investigated whether systemic infusion of MSC-CM could lead to a hepatoprotective response in the acutely injured liver, specifically by inhibiting cell death and stimulating reparative programs. This group used a sub lethal regimen of D-galactosamine induction, demonstrating a significant survival benefit and prevention of liver enzyme release after MSC-CM treatment.

In view of the above mentioned disadvantages of stem cell treatments, the fact that prior art highly efficient preparations in the field of regenerative medicine usually contain cells is a technical problem which should be overcome.

Thus, the object of the present invention is to provide a preparation which is effective as a pharmaceutical composition in the field of regenerative medicine but which does not contain cells, thereby avoiding the drawbacks caused by the preparations of the prior art which contain cells, particularly stem cells.

Another object of the present invention is to provide a method of preparing a pharmaceutical composition which is effective in the field of regenerative medicine but which does not contain cells, thereby avoiding the drawbacks caused by the preparations of the prior art which contain cells, particularly stem cells.

These and other objects are achieved by the preparations and the method as defined in the independent claims. Dependent claims are directed to preferred embodiments of the invention. The subject-matter of both dependent and independent claims forms an integral part of the description.

Using a mouse model of fulminant hepatic failure (FHF), the cell-free conditioned medium (cell-free CM) produced by culturing a liver progenitor cell line, such as e.g. the non-oval human liver pluripotent progenitor cell line disclosed in WO2006/126236, was shown by the inventors to exert a regenerative effect on the liver. The cell-free conditioned medium (cell-free CM) produced by culturing the liver progenitor cell line was shown to be effective in the therapy of organ failure, in particular in the therapy of liver and kidney failure. Surprisingly, it was also found that a liver progenitor cell line-CM is significantly more effective than a mesenchymal stem cell-CM prepared under the same conditions.

In particular, in the studies described in example 1 of the present description, 6- to 7-week-old male SCID mice were given an intraperitoneal injection of 500 μL saline containing 0.125 μg LPS and 18 mg D-Galactosamine (GalN) to induce FHF. After 30 minutes, 1 and 3 hours after LPS and GalN administration, mice were injected intraperitoneally with 3 ml of conditioned medium derived from HLSCs cultured in a rotary bioreactor. Preliminary analysis of the conditioned medium revealed a large fraction of cytokines, chemokines and growth factors. Serum levels of alanine transaminase and aspartate transaminase markedly increased after injury induction and significantly decreased after 6 days of injection with conditioned medium treatments. On the other hand, histopathological analysis of liver tissue evaluated by BrdU, PCNA and Tunel assay revealed a decreased index of apoptosis and necrosis and a recovery of tissue morphology.

These studies provided the first experimental evidence of potential therapeutic use of HLSCs-derived conditioned medium in the treatment of inflammatory conditions and organ regeneration.

Thus, a first aspect of the invention is a preparation consisting of a cell-free conditioned medium obtainable by culturing a liver progenitor cell line, preferably a non-oval human liver pluripotent progenitor cell line, more preferably the non-oval human liver pluripotent cell line disclosed in International patent application WO2006/126236, which is herein incorporated by reference.

A pharmaceutical composition comprising an effective amount of the preparation defined above also falls within the scope of the invention.

Figure 1:
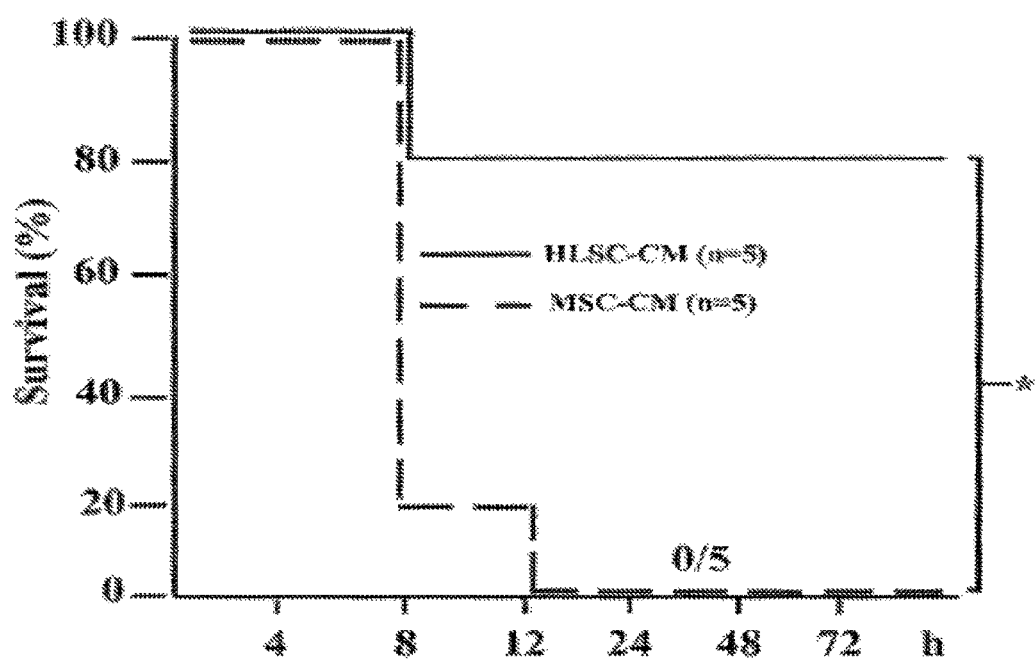
FIG. 1 graphically depicts test results showing mice survival rate (%) over time in LPS/GaIN lethal models treated with HLSC-derived CM or MSC-derived CM.

In the following, the cell-free conditioned medium derived from a liver progenitor cell line which forms the subject-matter of the invention shall be referred to as the "cell-free HLSC-CM".

The term "HLSC" refers to a liver pluripotent progenitor/stem cell line. Preferably, the term "HLSC" refers to a non-oval liver pluripotent cell line, more preferably to the liver pluripotent progenitor/stem cell line disclosed in WO2006/126236. More preferably, the HLSC cell line has the features defined in any of claims 1 to 10 of WO2006/126236 and/or the features summarised in Table I, page 7 of WO2006/126236. Such features are hereby incorporated by reference.

The cell-free HLSCs-CM which forms the subject-matter of the invention is suitable for use as a pharmaceutical composition as such or in a concentrated form. A concentrated form is concentrated for example at least approximately 5-fold, preferably at least approximately 10-fold, more preferably at least approximately 20-fold, even more preferably approximately 25-fold.

Preferably, the cell-free HLSC-CM of the invention is obtained from liver pluripotent progenitor/stem cells, preferably the HLSC cell line disclosed in WO2006/126236, cultured under GMP conditions, which are known to the skilled person. Alternatively, it may be obtained from liver pluripotent progenitor/stem cells, preferably the HLSC cell line disclosed in WO2006/126236, cultured in a BAL (Bio-Artificial Liver) system, which is also known to the skilled person.

An example of GMP conditions for growing liver pluripotent progenitor/stem cells and collecting the cell-free conditioned medium (CM) thereof is as follows:

Liver pluripotent progenitor/stem cells are isolated by the method disclosed in WO2006/126236, in which the expansion step is carried out by culturing the progenitor stem cells in the presence of foetal calf serum (FCS) preferably at a concentration of about 10%, hEGF (human epithelial growth factor) and bFGF (basic fibroblast growth factor). FCS, bFGF and hEGF are preferably GMP grade, e.g. those produced by Invitrogen.

For collecting the conditioned medium in GMP conditions, FCS is removed from the culture, since this is an heterologous protein that is not suitable for injection into humans. To that end, the cells are washed and cultured for 24 hours in a collecting medium comprised e.g. of alpha-MEM supplemented with GMP grade human albumin. Albumin is preferably at a concentration of about 0.05%. The cell-free conditioned medium is then collected by centrifugation or filtration.

In the in vivo experimentation mentioned above, the administration of the cell-free HLSC-CM of the invention to an animal model (SCID mice) of fulminant hepatic failure (FHF) was shown to provide a significant survival benefit over SCID mice treated with MSC-CM.

Thus, another aspect of the invention is a cell-free conditioned cell culture medium obtainable by culturing a liver progenitor cell line, preferably a non-oval human liver pluripotent progenitor cell line, even more preferably the non-oval human liver pluripotent cell line disclosed in International patent application WO2006/126236, for use as a medicament.

According to a preferred embodiment, the medicament is for the treatment of organ failure and/or injury, preferably liver and/or kidney failure and/or injury.

In addition, the inventors analysed the composition of the cell-free HLSC-CM of the invention, in order to identify those proteins (e.g. cytokines, chemokynes, growth factors and/or other proteins), which are more likely to provide a significant contribution to the CM's beneficial effects mentioned above, so as to provide simplified pharmaceutical compositions comprised of a protein mixture capable of mimicking, at least in part, the organ regenerating capabilities of the CM produced by culturing the HLSCs as described above.

Thus, another aspect of the invention is a simplified pharmaceutical composition comprising a pharmaceutically effective amount of a mixture of at least hepatocyte growth factor (HGF), interleukin 6 (IL-6) and interleukin 8 (IL-8).

In a preferred embodiment, the simplified pharmaceutical composition comprises a pharmaceutically effective amount of a mixture of at least hepatocyte growth factor (HGF), interleukin 6 (IL-6), interleukin 8 (IL-8) and vascular endothelial growth factor (VEGF).

In another preferred embodiment, the simplified pharmaceutical composition comprises a pharmaceutically effective amount of a mixture of at least hepatocyte growth factor (HGF), interleukin 6 (IL-6), interleukin 8 (IL-8) and macrophage stimulating protein (MSP) and optionally vascular endothelial growth factor (VEGF).

In yet another preferred embodiment, the simplified pharmaceutical composition comprises a pharmaceutically effective amount of a mixture of proteins according to any of the embodiments defined above and at least one further protein selected from the group consisting of Activin C, Activated leukocyte cell adhesion molecule (ALCAM), Chemokine (C-C motif) receptor 4 (CCR4), Cysteine rich transmembrane BMP regulator 1 (chordin-like) (CRIM), Decorin, Ectodysplasin A2 (EDA-A2), Endothelin, Fibroblast growth factor receptor-like 1 (FGF R5), Glypican 3, growth-related oncoprotein (GRO), insulin-like growth factor binding protein 6 (IGFBP-6), insulin-like growth factor 1 (IGF-1), Interleukin 20 receptor, alpha (IL-20 R alpha), kringle containing transmembrane protein 2 (Kremen-2), latent transforming growth factor beta binding protein 1 (Latent TGF-beta bp1), major intrinsic protein of lens fiber (MIP-2), MSP beta-chain, Osteoprotegerin/TNFRSF11B (tumor necrosis factor receptor superfamily, member 11b), soluble gp130 (sgp130), secreted protein, acidic, cysteine-rich (osteonectin) (SPARC).

The preferred cytokine concentration ranges in the simplified pharmaceutical composition of the invention are as follows:
  HGF: 1-100 ng/ml, preferably 5-80 ng/ml, more preferably 10-65 ng/ml;
  IL-6: 10-200 ng/ml, preferably 20-100 ng/ml, more preferably 30-50 ng/ml;
  IL-8: 35 ng/ml, preferably 50-600 ng/ml, more preferably 100-300 ng/ml;
  VEGF (if present): 10-400 ng/ml, preferably 20-250 ng/ml, more preferably 35-175 ng/ml; and
  MSP (if present): 1-100 pg/ml, preferably 5-80 pg/ml, more preferably 5-65 pg/ml.

However, the scope of the invention also includes any diluted or concentrated form of the simplified pharmaceutical composition. A concentrated form is concentrated for example at least approximately 5-fold, preferably at least approximately 10-fold, more preferably at least approximately 20-fold, even more preferably approximately 25-fold. A diluted form is diluted for example at least approximately 5 fold, preferably at least approximately 10 fold, more preferably at least approximately 20 fold, even more preferably at least approximately 25 fold.

The simplified pharmaceutical composition of the invention in suitable for use as a medicament, particularly for the treatment of organ failure and/or injury, preferably liver and/or kidney failure and/or injury. According to a preferred embodiment, the pharmaceutical composition is formulated so as to administer the following cytokine doses:
  HGF: 0.01-1 mg/kg, preferably 0.03-0.8 mg/kg, more preferably 0.1-0.5 mg/kg;
  interleukin 6 (IL-6): 0.01-1 mg/kg, preferably 0.03-0.8 mg/kg, more preferably 0.05-0.5 mg/kg;
  interleukin 8 (IL-8): 0.01-1 mg/kg, preferably 0.02-0.8 mg/kg, more preferably 0.03-0.5 mg/kg;
  VEGF (if present): 0.01-1 mg/kg, preferably 0.02-0.8 mg/kg, more preferably 0.04-0.5 mg/kg;
  MSP (if present): 0.01-1 mg/kg, preferably 0.02-0.8 mg/kg, more preferably 0.08-0.5 mg/kg.

In a particularly preferred embodiment these cytokine doses are administered once per day.

It is to be understood that the above defined simplified pharmaceutical compositions are provided purely as non-limiting examples of simplified pharmaceutical compositions capable of mimicking, at least in part, the organ regenerating capabilities of a CM obtainable by culturing HLSCs as described above.

Further objects and advantages of the invention will more clearly appear from the following examples, which are provided purely by way of illustration.

It is also to be understood that further embodiments of the claimed pharmaceutical compositions and methods may be envisaged based on the examples provided herein below, without departing from the scope of the invention.

Example 1—Preliminary In Vivo Studies

Preparation of HLSC and MSC Cells Cultures

Human liver progenitors cells (HLSCs) were isolated as described in WO2006/126236. The cells were allowed to grow at 60%-70% confluence (approximately $2 \times 10^6$ HLSCs per 75-cm$^2$ flask), washed thoroughly, and cultured in 10 mL serum-free alpha-MEM medium supplemented with 0.05% human serum albumin (GMP produced). Human mesenchymal stem cells (MSCs) were isolated from bone marrow aspirates and grown and characterized as previously reported. MSCs were cultured in MesenPRO RS™ Medium which is a reduced serum (2% FCS) medium specifically formulated to support the growth of MSCs.

Preparation of Conditioned Medium

Cell free conditioned medium were prepared by collecting the medium after 24 hours of culture of MSCs and HLSCs by centrifugation. The experiments were performed with a cell mass of $2 \times 10^6$ cells. The medium was then concentrated, approximately 25 fold, using ultrafiltration units (Amicon Ultra-PL 3, Millipore) with a 3 kDa molecular weight cut-off. A total of 250 μl of conditioned medium was obtained. This concentrated medium was diluted in 3 ml of α-MEM (without FCS) to a final volume of 3 ml. 1 ml of conditioned medium was administered intraperitoneally 30 minutes, 1 and 3 hours after induction of liver injury.

FHF In Vivo Model

For induction of fulminant hepatic failure (FHF), lethal toxicity of lipopolysaccharide (LPS) on treating animals with D-galactosamine (2-amino-2-deoxy-D-galactose) was developed as previously described (Lehmann V, Freudenberg M A, Galanos C. Lethal toxicity of ipopolysaccharide and tumor necrosis factor in normal and D-galactosamine-treated mice. J Exp Med. 1987; 165(3):657-63). Briefly, a group of 10 SCID mice received an intraperitoneal injection of D-galactosamine (GaIN) (600 mg/kg) and 0.125 μg of LPS per animal. The inventors previously determined that 100% lethality was induced in GaIN (600 mg/kg) and LPS (0.125 µg per animal) treated mice within 8 hours. GaIN and LPS were administered as a mixture in 500 µl of pyrogen-free NaCl solution. Deaths were recorded up to 24 hours after injection. 30 minutes, 1 and 3 hours after of LPS and GaIN injection, mice were intraperitoneally injected three times with 1 mL of HLSC and MSC concentrated conditioned medium. As shown in FIG. 1, four out of five mice injected with the HLSC-derived CM survived, while none of the mice treated with the MSC-derived CM survived.

Cytokine Composition of HLSC and MSC Conditioned Medium

For studying composition of conditioned medium obtained by culturing HLSCs and MSCs as disclosed above, a panel of 31 different cytokines was measured by multiple ELISA (Bioclarma). Both cells types were cultured in a medium with 10% FCS. Conditioned media were collected after 24 hours of culture. The cytokine composition of medium alone was also measured. The results are provided below in Table 1.

TABLE 1

HLSCs vs. MSCs: CYTOKINE PRODUCTION*

|  | HLSCs | MSCs | 10% FCS culture condition |
|---|---|---|---|
| IL1β | 0 | 0 | 0.86 |
| ILra | 0 | 0 | 0 |
| IL-2 | 0 | 0 | 0 |
| IL-4 | 0 | 0 | 0.73 |
| IL-5 | 0 | 0 | 0 |
| IL-6 | 1130.89 | 2434.4 | 0 |
| IL-7 | 0 | 0 | 0 |
| IL-8 | >4205.64 | 51.65 | 0.36 |
| IL-9 | 0 | 0 | 0 |
| IL-10 | 0.12 | 0.36 | 0.85 |
| IL-12 | 0 | 0.47 | 0.24 |
| IL-13 | 0 | 0 | 0 |
| IL-15 | 0 | 0 | 0 |
| IL-17 | 0 | 0 | 0 |
| Eotaxin | 5.1 | 3.96 | 0 |
| bFGF | 0 | 0 | 0 |
| G-CSF | 43.17 | 11.06 | 0 |
| GM-CSF | 1.75 | 0 | 0.03 |
| IFNγ | 38.46 | 104.73 | 0 |
| IP-10 | 0 | 0 | 0 |
| MCP-1 | 514.43 | 256.03 | 0 |
| MIP-1α | 0 | 0 | 0 |
| MIP-1β | 0 | 0 | 0 |
| PDGF | 0 | 0 | 0 |
| Rantes | 5.97 | 0 | 0 |
| TNFα | 3.7 | 13.04 | 0.19 |
| VEGF | 896.9 | 4961.43 | 0 |
| HGF | 5179 | 2.3 | 0 |
| M-CSF | 17.79 | 4.48 | 0 |
| MIF | 159.26 | 32.51 | 5.29 |
| SCF | 5.1 | 0.11 | 0 |

*(cytokine concentration was expressed in pg/ml × $10^6$ cells of both HLSC and MSC cultured in 10% FCS culture condition for 24 hours)

Example 2—Effect of HLSCs and MSCs-CM Obtained from T-Flask Culture and of Protein Mixtures in a D-galactosamine/endotoxin In Vivo Model of (FHF)

The following experimental studies in an in vivo model (SCID mice) of fulminant hepatic failure (FHF) were carried out.

1) The first experimental protocol consisted in the intraperitoneal injection of 1 ml of a 25-fold concentrated supernatant obtained from HLSC T-flask culture. 25-fold concentration was achieved with 3 KD membranes (Millipore). The supernatant was subjected to ultracentrifugation before use. The injection was administered 30 minutes, 1 hour and 3 hours after FHF induction by D-GaIN/LPS injection. Twelve SCID mice were treated in total.

2) The second experimental protocol consisted in the injection of a cytokine mixture. A total of 10 SCID mice were injected with the following recombinant cytokine mixture. HGF: 870.75 ng/ml×30 ml of alpha-MEM (i.v. injections)=26 µg IL-6: 340.5 ng/ml×30 (i.v. injections) =10.4 µg IL-8: 261 ng/ml×30 (i.v. injections)=8 µg VEGF: 202 ng/ml×30 (i.v. injections)=6 µg. 30 ml of this mixture were prepared in order to have 3 ml of mixture for a total of 10 SCID mice. Each SCID mice was injected with 1 ml of this mixture of cytokines at 30 minutes, 1 hour and 3 hours after GALN/LPS intraperitoneal injection. Each SCID mice received: [HGF]: 2.59 µg, [IL-6]: 1.02 µg, [IL-8]: 0.79 µg, [VEGF]: 0.6 µg. This mixture is designated as MIX 4.

3) The third experimental protocol consisted in the injection of MIX 4 plus MSP-1. A total of 5 SCID mice were injected. Each SCID mice received: [HGF]: 2.59 µg, [IL-6]: 1.02 µg, [IL-8]: 0.79 µg, [VEGF]: 0.6 µg (which are the concentration of cytokine obtained from BAL experiments) plus [MSP-1]: 2 ug.

4) The fourth experimental protocol consisted in the injection of MSC-CM or HLSC-CM. In order to obtain MSCs-CM, MSCs were allowed to grow to 90% confluence (approximately $2\times10^6$ MSCs per 75-cm$^2$ flask), washed thoroughly and cultured in 10 mL MesenPRO RS™, a 2% FCS cultured medium. Conditioned medium was collected 24 hours later and concentrated 25-fold using ultrafiltration units (Millipore, Bedford, Mass.) with a 3-kDa cut-off. To produce HLSCs-CM, HLSCs were allowed to grow to 60% to 70% confluence (approximately $2\times10^6$ HLSC per 75-cm$^2$ flask), washed thoroughly, and cultured in 10 mL serum-free alpha-MEM medium supplemented with 0.05% human serum albumin (GMP produced). Conditioned medium was collected 24 hours later and concentrated 25-fold using ultrafiltration units (Millipore, Bedford, Mass.) with a 3-kDa cut-off.

The mean weight of the SCID mice used in these experiments was of about 25 g.

Materials and Methods

FHF In Vivo Model.

For FHF induction, lethal toxicity of lipopolysaccharide (LPS) on treating animals with D-galactosamine (2-amino-2-deoxy-D-galactose) was developed as previously described (Lehmann V, Freudenberg M A, Galanos C. Lethal toxicity of lipopolysaccharide and tumor necrosis factor in normal and D-galactosamine-treated mice. J Exp Med. 1987; 165(3):657-63). Briefly, SCID mice received an intraperitoneal injection of D-galactosamine (GaIN) (600 mg/kg, 18 mg per animal) and 0.125 µg of LPS per animal. The inventors previously determined that 100% lethality was induced in GaIN (600 mg/kg) and LPS (0.125 µg per animal) treated mice within 8 hours. GaIN and LPS were administered as a mixture in 500 µl of pyrogen-free NaCl solution. Deaths were recorded up to 24 hr after injection. 30 minutes, 1 and 3 hours after of LPS and GaIN injection, mice were intraperitoneally injected with 1 mL of HLSC-conditioned medium, MSC-conditioned medium or cytokine mixture.

Cell Culture.

Human mesenchymal stem cells (MSCs) were isolated from bone marrow aspirates and grown and characterized as previously reported. MSCs were cultured in MesenPRO RS™ Medium which is a reduced serum (2% FCS) medium specifically formulated to support the growth of MSC. Cells were used for experiments during passages 3-5.

MSCs-Conditioned Medium (CM) Preparation.

Human MSCs were cultured and characterized for surface marker expression and adipogenic and osteogenic differentiation ability as described previously. To obtain MSCs-CM, cells were allowed to grow to 90% confluence (approximately $2 \times 10^6$ MSCs per 75-cm$^2$ flask), washed thoroughly and cultured in 10 mL MesenPRO RS™, a 2% FCS cultured medium. Conditioned medium was collected 24 hours later and concentrated 25-fold using ultrafiltration units (Millipore, Bedford, Mass.) with a 3-kDa cut-off.

HLSCs-Cm Preparation.

Human HLSCs were obtained from frozen human hepatocyte. HLSCs were cultured and characterized for surface marker expression and differentiation ability as described previously. To obtain HLSCs-CM, cells were allowed to grow to 60% to 70% confluence (approximately $2 \times 10^6$ HLSC per 75-cm$^2$ flask), washed thoroughly and cultured in 10 mL serum-free alpha-MEM medium supplemented with 0.05% human serum albumin (GMP produced). Conditioned medium was collected 24 hours later and concentrated 25-fold using ultrafiltration units (Millipore, Bedford, Mass.) with a 3-kDa cut-off.

Concentration of Conditioned Medium:

Supernatants were collected from T-flask after 24 hours of culture. The supernatant was then concentrated, approximately 25 fold, using ultrafiltration units with a 3 KDa molecular weight cut-off from Millipore.

Histological Analysis:

Necrosis of liver were analyzed through H&E staining (Hematoxylin and Eosin staining), proliferation (PCNA staining) and TUNEL (apoptotic cells).

Biochemical Analyses.

Serum alanine transaminase (ALT) and aspartate transaminase (AST) levels were measured using a standard clinical automatic analyzer.

Western Blot:

Western Blot was performed for detection of BAX and BclXS/L. Livers were homogenized and lysed at 4° C. for 1 hour in lysis buffer (50 mmol/L Tris-HCl, pH 8.3, 1% Triton X-100, 10 µmol/L phenylmethyl sulfonyl fluoride, 10 µmol/L leupeptin, and 100 U/ml aprotinin) and centrifuged at 15,000 g. The protein contents of the supernatants were measured by the Bradford method. Aliquots containing 200 µg of protein of livers lysates were subjected to 10% sodium dodecyl sulfate-polyacrylamide gel electrophoresis under reducing conditions and electro blotted onto nitrocellulose membrane filters. The blots were blocked with 5% nonfat milk in 20 mmol/L Tris-HCl, pH 7.5, 500 mmol/L NaCl plus 0.1% Tween (TBS-T). The membranes were subsequently immunoblotted overnight at 4° C. with the relevant primary antibodies at the appropriate concentration. After extensive washings with TBS-T, the blots were incubated for 1 hour at room temperature with peroxidase-conjugated isotype-specific secondary antibodies, washed with TBS-T, developed with ECL detection reagents for 1 minute, and exposed to X-Omat film. The following antibodies were used: anti-BAX monoclonal antibody and anti-BclXS/L polyclonal antibody from Santa Cruz Biotechnology.

Results

Figure 2:
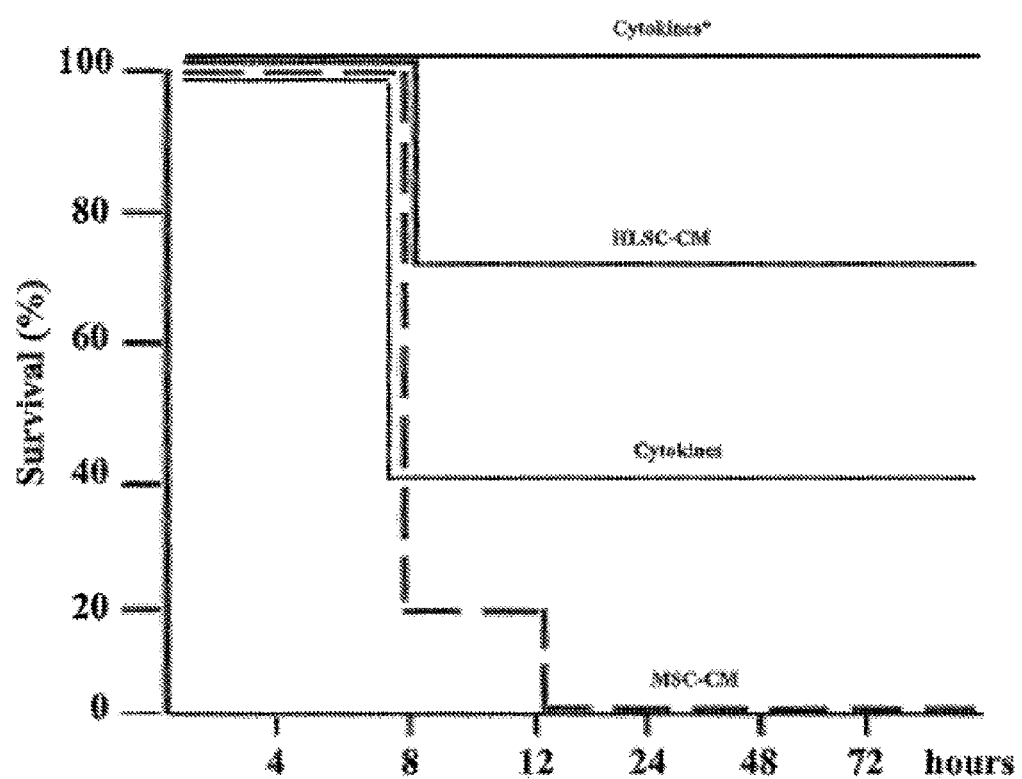
FIG. 2 graphically depicts test results showing mice survival rate (%) over time in LPS/GaIN lethal models treated with HLSC-CM, MSC-CM, a cytokine mixture, or the cytokine mixture plus MSP-1.
Figure 3:
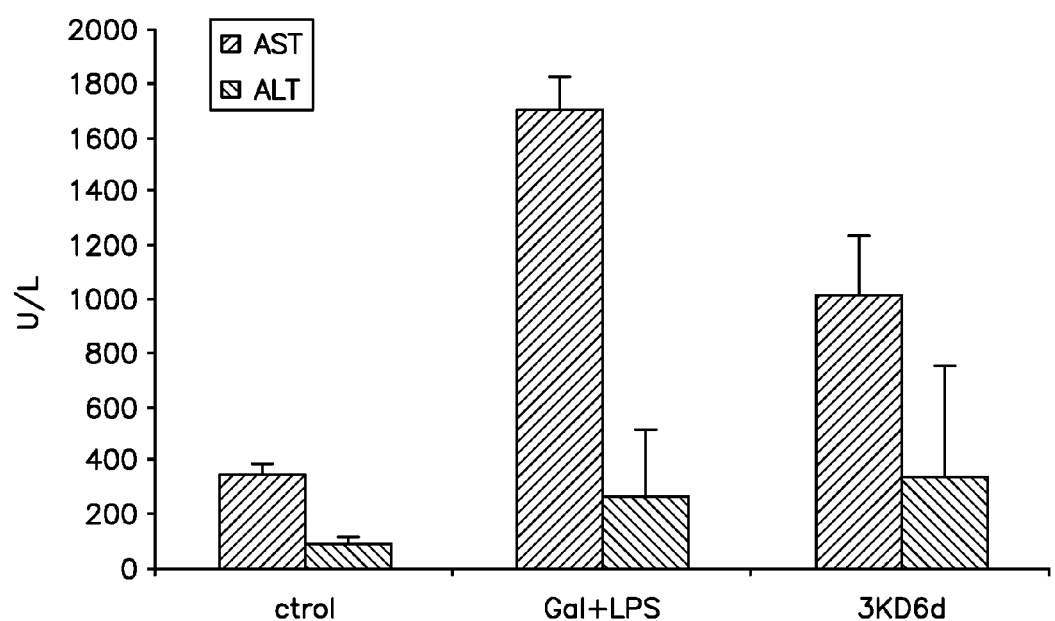
FIG. 3 graphically depicts test results showing AST and ALT serum levels of control, GaIN/LPS and GaIN/LPS treated mice injected with HLSC-CM after 6 days of FHF induction.
Figure 4:
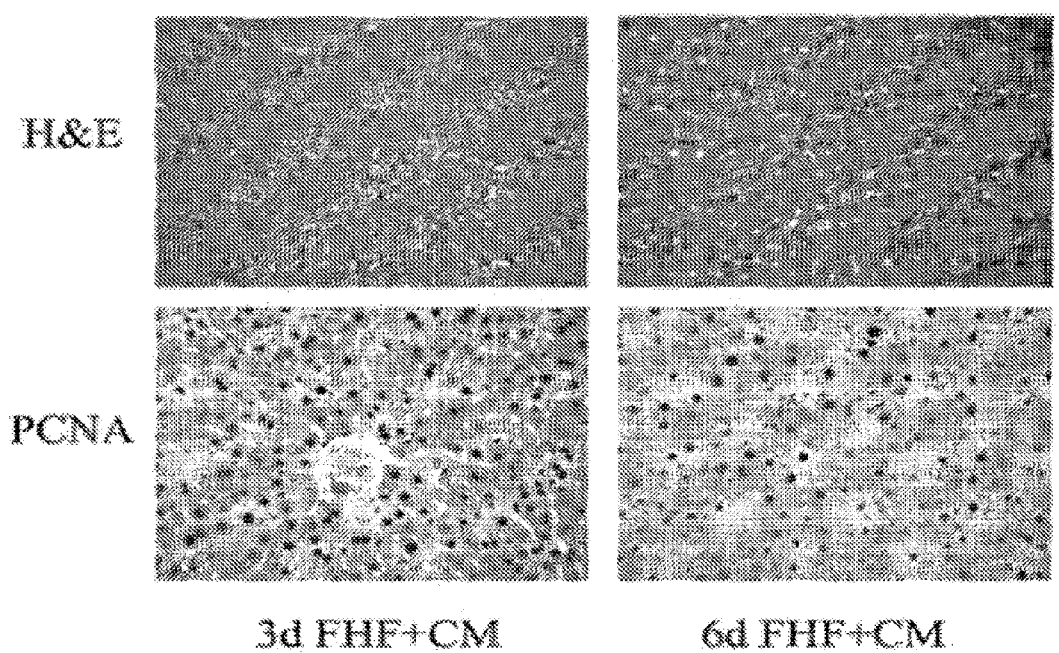
FIG. 4 contains pictures showing the H&E and PCNA staining of GaIN/LPS treated SCID mice injected with HLSC-CM after 3 and 6 days of FHF induction.

The results obtained are illustrated in FIGS. 2-4.

FIG. 2 shows the survival rate (%) of GaIN/LPS injured-SCID mice treated with HLSC-CM (n=22; 73% of survival), MSC-CM (n=5; 0% of survival) or with a cytokine mixture (cytokines: VEGF,IL6,IL8,HGF; n=10; 40% of survival, and the cytokine mixture plus MSP-1(cytokines*: VEGF,IL6, IL8,HGF+MSP-1; n=5; 100% of survival).

FIG. 3 shows the Aspartate aminotransferase (AST) and alanine aminotransferase (ALT) serum levels of control, GaIN/LPS and GaIN/LPS treated mice injected with HLSC-CM after 6 days of FHF induction.

FIG. 4 is a picture showing the H&E and PCNA staining of GaIN/LPS treated SCID mice injected with HLSC-CM after 3 and 6 days of FHF induction.

Example 3—In Vitro Experiments Using HLSCs- and MSCs-Conditioned Medium (CM) and Cytokine Mixtures In this experimental protocol, the ability of HLSCs-CM to directly inhibit apoptosis in cultured human primary hepatocyte was investigated. Using in vitro assays of apoptosis, the conditioned medium derived from HLSCs was demonstrated to exert a direct inhibitory effect on hepatocyte death. This in vitro activity was also compared to the in vitro activity of MSCs-CM. The effect of 6 human recombinant cytokines present in the conditioned medium produced by the cells was also studied in human hepatocyte apoptosis assays.

Materials and Methods

Cell Culture.

Human mesenchymal stem cells (MSCs) were isolated from bone marrow aspirates, grown and characterized as previously reported. MSCs were cultured in MesenPRO RS™ Medium which is a reduced serum (2% FCS) medium specifically formulated to support the growth of MSCs. Cells were used for experiments during passages 3-5. Human liver progenitors cells (HLSCs) were isolated as previously described and cultured in alpha-MEM/EBM (3:1) containing 10% of FCS (GMP; foetal calf serum) supplemented with 4 ng/ml of both hEGF and hFGF.

MSCs-Conditioned Medium (CM).

Human MSCs were cultured and characterized for surface marker expression and adipogenic and osteogenic differentiation ability as described previously. To obtain MSCs-CM, cells were allowed to grow to 90% confluence (approximately $2 \times 10^6$ MSCs per 75-cm$^2$ flask), washed thoroughly, and cultured in 10 mL MesenPRO RS™, a 2% FCS cultured medium. Conditioned medium was collected 24 hours later, subject to ultracentrifugation and concentrated 25-fold using ultrafiltration units (Millipore, Bedford, Mass.) with a 3-kDa cut-off.

HLSCs-CM.

Human HLSCs were obtained from frozen human hepatocytes. HLSCs were cultured and characterized for surface marker expression and differentiation ability as described previously. To obtain HLSCs-CM, the cells were allowed to grow to 60% to 70% confluence (approximately $2 \times 10^6$ HLSC per 75-cm$^2$ flask), washed thoroughly, and cultured in 10 mL serum-free alpha-MEM medium supplemented with 0.05% human serum albumin (GMP produced). The conditioned medium was collected 24 hours later, subject to ultracentrifugation and concentrated 25-fold using ultrafiltration units (Millipore, Bedford, Mass.) with a 3-kDa cut-off.

Hepatocyte Apoptosis In Vitro (TUNEL).

Hepatocytes were cultured for 1 day in 96-well plates at 30000 cells/well in fibronectin coated plates. Galactosamine-D was added at a concentration of 5 mM for 24 hour, followed by different doses of conditioned media derived from HLSC and MSC obtained as previously described (from 0.5% to 16%), mixture of four cytokines (MIX 4 stands for IL-8, IL-6, HGF, VEGF). Results are expressed as mean±SD of 8 different experiments.

Cytokine Concentration.

The concentration of the human recombinant cytokines used in the in vitro experiments was selected from the concentrations produced by HLSCs after 24 hours in flask culture conditions, concentrated 25 fold. In the case of MSP, the concentration obtained in BAL culture conditions was used. The first concentration is considered the same as the stock of conditioned medium, the cells were then stimulated with the 16% of each stock concentration which represented the highest concentration of the conditioned medium used in vitro.

IL-6=56.5 ng/ml, final concentration used=9 ng/ml
IL-8=210 ng/ml, final concentration used=33.6 ng/ml
HGF=259 ng/ml, final concentration used=41.4 ng/ml
VEGF=44.8 ng/ml, final concentration used=7.2 ng/ml
MCP-1=25.7 ng/ml, final concentration used=4.1 ng/ml
MSP=60 ng/ml, final concentration used=9.6 ng/ml The results are illustrated in FIGS. 5-10.

Figure 5:
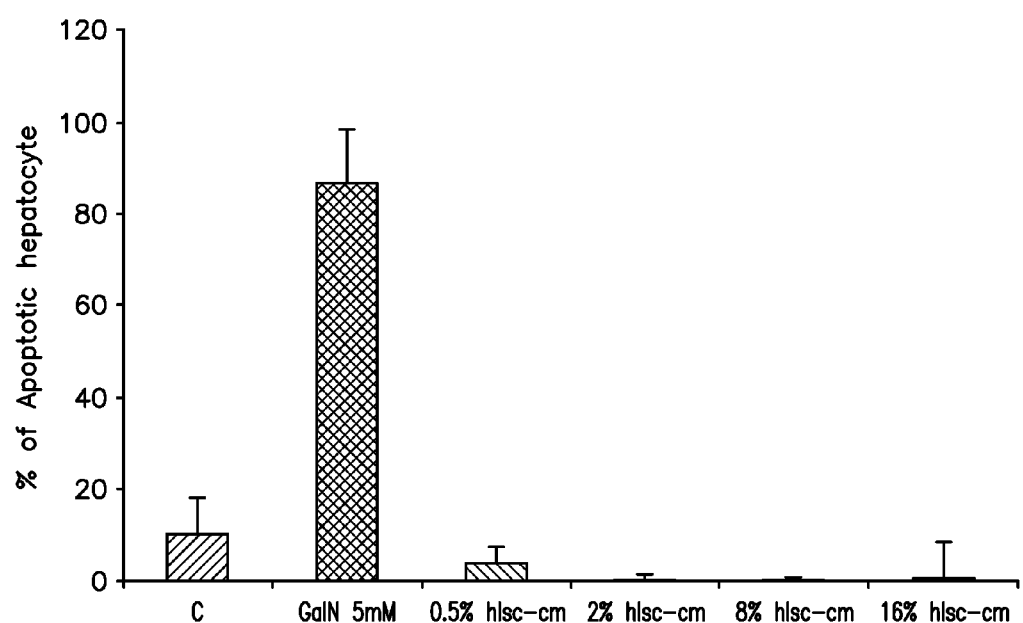
FIG. 5 graphically depicts test results showing hepatocyte apoptosis in vitro inhibition by HLSCs-CM at low concentrations.

FIG. 5 shows hepatocyte apoptosis in vitro inhibition by HLSCs-CM at low concentrations. Primary human hepatocytes were cultured in fibronectin coated plates. Apoptosis was induced with D-Galactosamine (GalN). During exposure to GalN, hepatocytes were cultured in a cell culture medium supplemented with 0.5; 2; 8 or 16% of 25-fold concentrated HLSCs-CM (GMP produced). Cell death was quantified using digital image analysis of four images per well. The data shown are mean±SD of 8 experiments. P<0.05.

Figure 6:
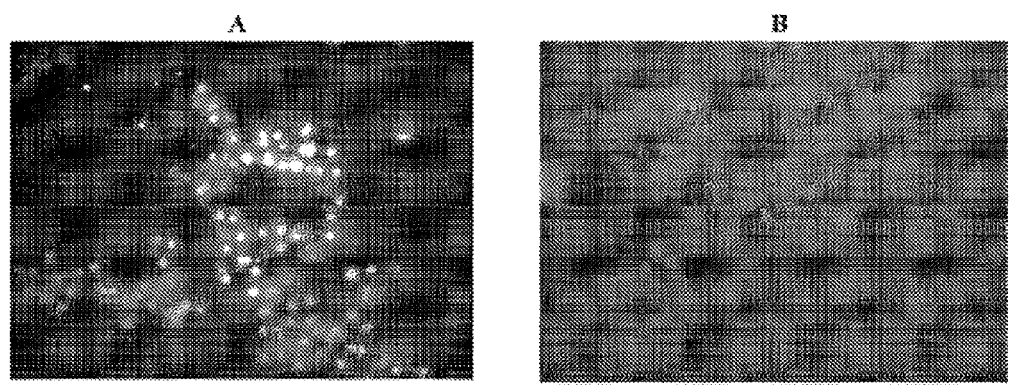
FIG. 6 shows representative micrographs of TUNEL assays of GaIN-treated human hepatocytes. (A) 5 mM GaIN-treated hepatocytes after 24 hours and (B) 5 mM GaIN-treated hepatocytes stimulated with 2% HLSCs-CM after 24 hours.

FIG. 6 shows representative micrographs of TUNEL assay of GalN-treated human hepatocytes. (A) 5 mM GalN-treated hepatocytes after 24 hours and (B) 5 mM GalN-treated hepatocytes stimulated with 2% HLSCs-CM after 24 hours.

Figure 7:
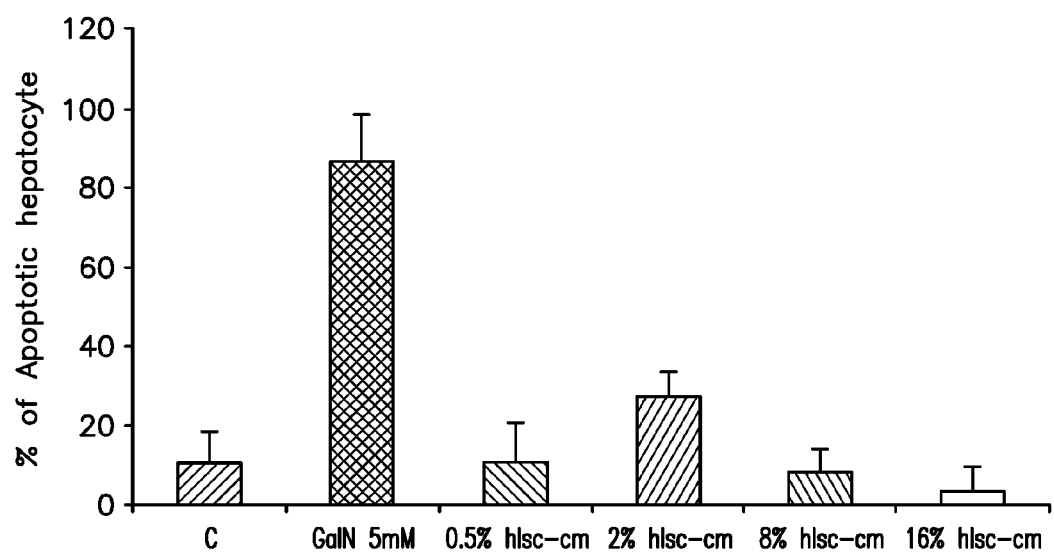
FIG. 7 graphically depicts test results showing hepatocyte apoptosis in vitro inhibition by MSCs-CM at low concentrations.

FIG. 7 shows hepatocyte apoptosis inhibition in vitro by MSCs-CM at low concentrations. Primary human hepatocytes were cultured in fibronectin coated plates. Apoptosis was induced with D-Galactosamine (GalN). During exposure to GalN, hepatocytes were cultured in a cell culture medium supplemented with 0.5; 2; 8 or 16% of 25-fold concentrated MSCs-CM. Cell death was quantified using digital image analysis of four images per well. The data shown are mean±SD of 8 experiments. P<0.05.

Figure 8:
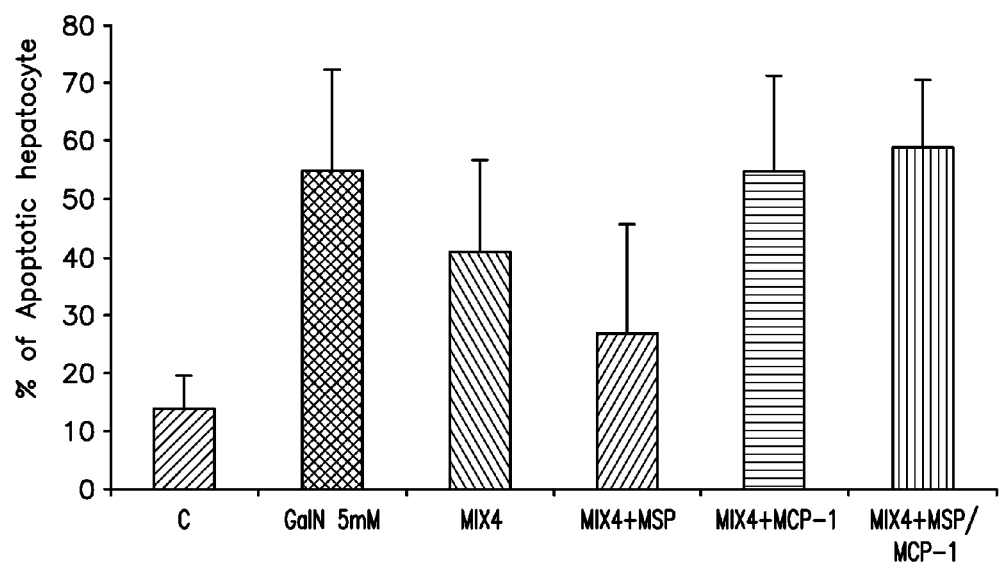
FIG. 8 graphically depicts test results showing hepatocyte apoptosis in vitro inhibition by various cytokine mixtures.

FIG. 8 shows hepatocyte apoptosis inhibition in vitro by various cytokine mixtures. Human hepatocytes were cultured in the presence of D-Galactosamine (GalN; 5 mM) for 24 hours. The use of MIX4+MSP on GalN-treated hepatocytes resulted in apoptosis inhibition after 24 hours. Hepatocytes treated with GalN were also cultured with MIX4+MCP-1 or with the combination of the MIX4+MSP+MCP-1. Cell death was quantified using digital image analysis of four images per well. The data shown are mean±SD of 8 experiments. *P<0.05.

Example 4—CM Composition Analysis by Multiplex and Enzyme-Linked Immunosorbant Assay Soluble cytokines produced into the culture media by human liver stem cells (HLSCs) have been shown to enhance liver healing. In order to further elucidate the mechanisms involved, the cytokines released by HLSCs were determined and compared to the cytokines produced by human bone marrow mesenchymal stem cells (MSCs). The analysis of the profile of the secreted cytokines was extended by the production of conditioned medium under different cell culture conditions, such as roller bottle, T-flask in normoxic conditions and T-flask under hypoxic conditions. In the case of MSCs, cells were culture only in T-flask in normoxic culture conditions. A total of 16 different conditioned media was obtained. All the analyses done with Multiplex system (from Bio-rad) of the conditioned medium produced in 24 hours of culture by HLSCs and MSCs, indicated the presence of cytokines and chemokines, such as major amounts of, inter alia, HGF, IL6, IL8, VEGF, MCP1, with a total of 31 different proteins. Several antibodies used for the Bio-Rad human multiplex assay were also assessed by ELISA (IL-6, IL-8, HGF, VEGF, MCP1 and MSP1). The ELISA was carried out with RayBio® Human ELISA kits according to the manufacturer's instructions. The inventors also comparatively assessed the multiplex and the enzyme-linked immunosorbant assay (ELISA). The comparison was based on the measurement of six cytokines present in the 16 different conditioned media produced. The cytokine concentrations, as measured by the different kits, showed similar trends, although the absolute concentrations measured were different.

Materials and Methods

Cell Culture

HLSCs.

Human liver progenitors cells (HLSC) were isolated as previously described and cultured in alpha-MEM/EBM (3:1) containing 10% of FCS (GMP; fetal calf serum) supplemented with 4 ng/ml of both rhEGF and rhFGF.

Initial cellular seeding and media compositions, for conditioned medium (CM) collection, in of all the experiments carried out with HLSCs cultured for 24 hours, were as described below.

2 experiments with cells at passage 3 cultured in Roller bottle: 20×10$^6$ HLSC culture in 100 ml of RPMI+0.05% human albumin 2 experiments with cells at passage 10 cultured in Roller bottle: 20×10$^6$ HLSC culture in 100 ml of RPMI+0.05% human albumin 3 experiments with cells at passage 3 cultured in T-flask in normoxic conditions: 2×10$^6$ HLSC culture in 10 ml of RPMI+0.05% human albumin 3 experiments with cells at passage 10 cultured in T-flask in normoxic conditions: 2×10$^6$ HLSC culture in 10 ml of RPMI+0.05% human albumin 2 experiments with cells at passage 3 cultured in Hypoxic conditions in T-flask: 2×10$^6$ HLSC culture in 10 ml of RPMI+0.05% human albumin 2 experiments with cells at passage 10 cultured in Hypoxic conditions in T-flask: 2×10$^6$ HLSC culture in 10 ml of RPMI+0.05% human albumin hMSCs.

Human mesenchymal stem cells (hMSCs) were isolated from human bone marrow aspirates and grown and characterized as previously reported. MSCs were cultured in MesenPRO RS™ Medium which is a reduced serum (2% FCS) medium specifically formulated to support the growth of MSCs. Cells were used for experiments during passage 3.

Initial cellular seeding and media compositions, for conditioned medium (CM) collection, of the experiments carried out with hMSCs cultured for 24 hours were as disclosed below.

2 experiments with cells at passage 3 cultured in T-flask in normoxic conditions: $2 \times 10^6$ in 10 ml of RPMI+ 0.05% human albumin Preparation of CM.

HLSCs-derived CM were obtained by seeding the cells at a concentration of $2 \times 10^6$ in T-flask and incubating them overnight into the incubator. The day after, cells were washed thoroughly, and cultured in 10 mL of RPMI (without phenol red) in the presence of 0.05% of human albumin. CM medium was collected 24 hours later and all the aliquots from every experiment were frozen at −20° C. CM was concentrated by centrifugation for 1, 30 hours at 4° C., at 2700 g using the ultrafiltration units from Millipore with a 3-kDa cut-off of pore sizes.

hMSCs-derived CM were obtained by allowing to grow to 90% confluence (approximately $2 \times 10^6$ MSCs per 75-cm$^2$ flask), washing thoroughly, and culturing in 10 mL of RPMI (without phenol red) in the presence of 0.05% of human albumin. Conditioned medium was collected 24 hours later and all the aliquots from each experiment were frozen at −20° C. CM was concentrated by centrifugation for 1, 30 hours at 4° C. at 2700 g, using the ultrafiltration units from Millipore with a 3-kDa cut-off of pore sizes.

After collection of CM, cells were recovered, cell viability was assessed by tryplan blue dye exclusion obtaining more than 95% of viability in all the experiments.

Total Protein Quantization.

Total protein concentration in CM was determined according to the Bradford method (Bio-Rad Laboratories) following the manufacturer's protocol. Bovine serum albumin (BSA) was used to create a standard reference. 5 µl from each sample was added to 1 ml of dye from the Bradford reagent diluted 1 to 5 with distilled water and mixed. After incubation for 5 min at room temperature, absorbance at 595 nm optic light was detected with a fluorophotometer. The protein concentration from each sample was calculated according to the linearized BSA absorbance curve.

ELISA.

The RayBio® Human ELISA (Enzyme-linked Immunosorbent Assay) for the quantitative measurement of IL-8, IL-6, VEGF, HGF, MCP1 and MSP1 was used. This assay employs antibodies specific for the human cytokines mentioned, coated on a 96-well plate. Standards and samples are pipetted into the wells and cytokines present in a sample is bound to the wells by the immobilized antibodies. The wells are washed and biotinylated anti-human cytokine antibodies are added. After washing away unbound biotinylated antibodies, HRP-conjugated streptavidin is pipetted to the wells. The wells are again washed, a TMB substrate solution is added to the wells and color develops in proportion to the amount of cytokines bound. The Stop Solution changes the color from blue to yellow, and the intensity of the color is measured at 450 nm.

Bioclarma Assay.

A multiplex biometric immunoassay from Bio-rad, containing fluorescent dyed microspheres conjugated with a monoclonal antibody specific for the target proteins, was used for cytokine measurement according to the manufacturer's instructions (Bio-Plex Human Cytokine Assay; Bio-Rad). The following cytokines were assayed: IL-1β, IL-1ra, IL-2, IL-4, IL-5, IL-6, IL-7, CXCL8 (IL-8), IL-9, IL-10, HGF, M-CSF, MIF, SCF, PDGF, Rantes, VEGF, Eotaxin, bFGF, IP-10, IFNγ, IL-12 (p70), IL-13, IL-15, IL-17, granulocyte colony stimulating factor (G-CSF), granulocyte-monocyte colony stimulating factor (GM-CSF), monocyte chemoattractive protein (MCP-1), macrophage inflammatory protein (MIP-1β/CCL4), MIP-1α and TNF-α.

Briefly, 250 µl undiluted CM were incubated with antibody-coupled beads. Complexes were washed, then incubated with biotinylated detection antibody and, finally, with streptavidin-phycoerythrin prior to assessing cytokine concentration titers. A range of 1.95-40,000 pg/ml recombinant cytokines was used to establish standard curves and to maximize the sensitivity and the assay dynamic range. Cytokine levels were determined using a multiplex array reader from Luminex™ Instrumentation System. The concentration was calculated using software provided by the manufacturer. The results obtained are illustrated below in Tables 2-8.

TABLE 2

Number of cells recovered after 24 hours

| Cells | Quantity of cells after 24 h |
|---|---|
| HLSC Roller 3p | $4.25 \pm 0.49 \times 10^6$ |
| HLSC Roller 10p | $2.3 \pm 2.1 \times 10^6$ |
| HLSC Hyp 10p | $1.82 \pm 0.74 \times 10^6$ |
| HLSC Hyp 3p | $1.04 \pm 0.88 \times 10^6$ |
| HLSC Norm 10p | $2.56 \pm 0.79 \times 10^6$ |
| HLSC Norm 3p | $1.70 \pm 0.18 \times 10^6$ |
| Norm MSC 3p | $2.35 \pm 0.78 \times 10^6$ |

TABLE 3

Protein concentration of CM after 24 hour in culture and after concentration with Amicon filters.

| CM derived from: | Protein concentration of CM (mg/ml) ± SD | Protein concentration of CM after Amicon concentration (mg/ml) ± SD |
|---|---|---|
| HLSC Roller 3p | 0.36 ± 0.004 | 7.405 ± 0.106 |
| HLSC Roller 10p | 0.335 ± 0.021 | 7.37 ± 0.141 |
| HLSC Hyp 10p | 0.315 ± 0.021 | 7.68 ± 0.396 |
| HLSC Hyp 3p | 0.31 ± 0.013 | 7.55 ± 0.707 |
| HLSC Norm 10p | 0.29 ± 0.012 | 7.18 ± 0.490 |
| HLSC Norm 3p | 0.28 ± 0.078 | 7.72 ± 0.132 |
| Norm MSC 3p | 0.23 ± 0.042 | 7.75 ± 0.276 |

TABLE 4

Concentration of cytokines (pg/ml) determined by Multiplex (Bioclarma) (pg/ml ± SD)

| Cytokine | Roller 3p HLSC | Rolled 10p HLSC | Hyp 10p HLSC | Hyp 3p HLSC | Norm 10p HLSC | Norm 3p HLSC | Norm 3p MSC |
|---|---|---|---|---|---|---|---|
| IL1β | 22 ± 0.14 | 34 ± 13 | 30.8 ± 19.8 | 83.4 ± 32.5 | 17.1 ± 9.9 | 51.8 ± 35.9 | 7.5 ± 2.6 |
| ILra | 96 ± 0.32 | 87 ± 5 | 99.8 ± 26.5 | 163.4 ± 31.9 | 86.1 ± 7.9 | 91.7 ± 32.6 | 596 ± 404 |
| IL-2 | 0 | 0 | 0 | 0 | 0 | 0 | 0 |

TABLE 4-continued

Concentration of cytokines (pg/ml) determined by Multiplex (Bioclarma) (pg/ml ± SD)

| Cytokine | Roller 3p HLSC | Rolled 10p HLSC | Hyp 10p HLSC | Hyp 3p HLSC | Norm 10p HLSC | Norm 3p HLSC | Norm 3p MSC |
|---|---|---|---|---|---|---|---|
| IL-4 | 2.6 ± 0.02 | 2.8 ± 0.05 | 2.9 ± 1.1 | 4.8 ± 0.9 | 2.4 ± 0.3 | 2.4 ± 1.3 | 2 ± 1.4 |
| IL-5 | 0 | 0 | 0 | 0 | 0 | 0 | 0 |
| IL-6 | >40000 | >40000 | >40000 | >40000 | >40000 | >40000 | >40000 |
| IL-7 | 0 | 4.4 ± 2.5 | 8.4 ± 2.4 | 24.1 ± 7.9 | 7.4 ± 3.7 | 18.5 ± 9 | 7.6 ± 1.6 |
| IL-8 | >35000 | >35000 | >35000 | >35000 | >35000 | >35000 | >35000 |
| IL-9 | 52 ± 0.8 | 42 ± 3.6 | 32.7 ± 12.4 | 41.9 ± 15.2 | 24.6 ± 7.7 | 26.1 ± 4.8 | 27.9 ± 3.0 |
| IL-10 | 32 ± 3.9 | 33 ± 5.5 | 32.9 ± 0.1 | 36 ± 4.2 | 28.5 ± 3.7 | 31.3 ± 1.3 | 35.8 ± 7.9 |
| IL-12 | 59.1 ± 11 | 52.8 ± 11.6 | 56.7 ± 8.7 | 74 ± 6.6 | 56 ± 8.1 | 41.1 ± 17 | 36.6 ± 13 |
| IL-13 | 9.2 ± 2.2 | 7.7 ± 0.8 | 5.6 ± 2.1 | 7.8 ± 3.4 | 4.4 ± 2.0 | 2.2 ± 1 | 4.9 ± 1.3 |
| IL-15 | 93.3 ± 9.8 | 87.1 ± 8.3 | 94.6 ± 5.6 | 95.9 ± 13.4 | 93.9 ± 10.7 | 81.8 ± 9.7 | 64.5 ± 22 |
| IL-17 | 0 | 0 | 0 | 0 | 0 | 0 | 0 |
| Eotaxin | 81.3 ± 19 | 359 ± 227 | 2350 ± 532 | 2748 ± 76 | 1932 ± 133 | 2417 ± 453 | 21 ± 17 |
| bFGF | 49.8 ± 3.9 | 79 ± 14 | 30.1 ± 5.6 | 23.5 ± 2.8 | 44 ± 59 | 22.1 ± 26 | 6.7 ± 9.2 |
| G-CSF | 1150 ± 149 | 1714 ± 183 | 1371 ± 1670 | 16275 ± 8389 | 490 ± 468 | 2188 ± 921 | 359.3 ± 212 |
| GM-CSF | 47 ± 0.8 | 37.4 ± 5.6 | 49.5 ± 2.4 | 59 ± 51 | 38.8 ± 3.8 | 60.4 ± 21 | 65 ± 65 |
| IFNγ | 156 ± 1.6 | 168 ± 10.1 | 171 ± 49.8 | 236 ± 27 | 147 ± 14.5 | 176.1 ± 44 | 174.5 ± 38 |
| IP-10 | 0 | 54 ± 77 | 30 ± 42 | 61 ± 86 | 14.5 ± 25 | 283.5 ± 132 | 28043.3 ± 13513 |
| MCP-1 | ? | ? | 5622 ± 2131 | 2999 ± 494 | 4614 ± 872 | 5647.9 ± 2821 | 1410.5 ± 767 |
| MIP-1α | 3.6 ± 1.4 | 2.1 ± 0.4 | 2.6 ± 0.2 | 2.8 ± 2.3 | 2.1 ± 0.5 | 5.8 ± 0.5 | 12.5 ± 1.1 |
| MIP-1β | 0 | 0 | 0 | 0 | 0 | 0 | 0 |
| bbPDGF | 0 | 0 | 0 | 0 | 0 | 0 | 0 |
| Rantes | 109 ± 28 | 328 ± 227 | 279 ± 210 | 909 ± 566 | 576 ± 522 | 118 ± 24 | 11353 ± 9310 |
| TNFα | 22 ± 2 | 24 ± 4 | 29 ± 4 | 40.5 ± 7.7 | 22 ± 2.5 | 24.6 ± 6.7 | 30.2 ± 5.3 |
| VEGF | 33817 ± 6318 | 24814 ± 1567 | 22591 ± 7330 | 32286 ± 4297 | 14830 ± 3860 | 16664 ± 10951 | 16485 ± 3722 |
| HGF | 12238 ± 1109 | 6674 ± 2872 | 20901 ± 1033 | 15508 ± 1159 | 20642 ± 3543 | 15853 ± 4380 | 340 ± 145 |
| M-CSF | 555 ± 39 | 256 ± 26 | 496 ± 177 | 538 ± 299 | 649 ± 628 | 548 ± 33 | 173 ± 65 |
| MIF | 35047 ± 4014 | 45045 ± 1835 | 30773 ± 9632 | 24216 ± 11108 | 24719 ± 14645 | 17956 ± 4115 | 10512 ± 1367 |
| SCF | 119 ± 10 | 119 ± 64 | 209 ± 32 | 144 ± 31 | 265 ± 216 | 211 ± 79 | 15.4 ± 3.6 |

TABLE 5

Range of concentration in pg/ml (or ng/ml where indicated) determined by multiplex of all of the CM produced by HLSCs and MSCs at passage 3 (bioclarma).

| | HLSC | MSC |
|---|---|---|
| IL1β | 15.9-87.7 | 4.9-10.1 |
| ILra | 59.1-124.3 | 192-1000 |
| IL-2 | 0 | 0 |
| IL-4 | 0-3.7 | 0-3.4 |
| IL-5 | 0 | 0 |
| IL-6 | >40000 | >40000 |
| IL-7 | 6.7-27.9 | 6-9.2 |
| IL-8 | >35000 | >35000 |
| IL-9 | 21.3-30.9 | 19.8-30.9 |
| IL-10 | 12.9-32.6 | 15-43.7 |
| IL-12 | 20.9-58.1 | 21.9-49.6 |
| IL-13 | 0-3.2 | 0-6.2 |
| IL-15 | 57-91.4 | 25-109 |
| IL-17 | 0 | 0 |
| Eotaxin | 505-2870 | 10-38 |
| bFGF | 22-6055 | 0 |
| G-CSF | 1267-3109 | 11-571 |
| GM-CSF | 19.8-81.4 | 0-130 |
| IFNγ | 97-220 | 107-213 |
| IP-10 | 152-416 | 0.9-41.6 (ng/ml) |
| MCP-1 | 1658-8500 | 600-2296 |
| MIP-1α | 5.3-13 | 11.4-90 |
| MIP-1β | 4.4-6.2 | 0-1000 |
| bbPDGF | 0 | 0 |
| Rantes | 94-142 | 124-20700 |
| TNFα | 17.9-31.3 | 24.9-35.5 |
| VEGF | 34.9-91 (ng/ml) | 25.9-65.9 (ng/ml) |
| HGF | 11.5-20.2 (ng/ml) | 195-485 |
| M-CSF | 515-1072 | 91-238 |
| MIF | 9114-22100 | 8280-11900 |
| SCF | 128-290 | 9.9-19 |

TABLE 6

Concentration of cytokines (pg/ml) determined by RayBio ® Human ELISA

| Cytokine | Roller 3p HLSC | Roller 10p HLSC | Hypoxic 10p HLSC | Hypoxic 3p HLSC | Normoxic 10p HLSC | Normoxic 3p HLSC | Normoxic 3p MSC |
|---|---|---|---|---|---|---|---|
| VEGF | 154572 ± 3903 | 121884 ± 50131 | 153456 ± 3479 | 132132 ± 297 | 118708 ± 16848 | 118936 ± 56365 | 157896 ± 4811 |
| HGF | 33822 ± 823 | 24312 ± 3971 | 90540 ± 23215 | 49050 ± 9631 | 88488 ± 9267 | 51716 ± 12211 | 0 |
| MCP1 | 6383 ± 98 | 6397 ± 126 | 5966 ± 9 | 5635 ± 38 | 5823 ± 319 | 5680 ± 189 | 5497 ± 465 |
| MSP1 | 20.4 ± 14.4 | 6.4 ± 4.5 | 5.4 ± 4.2 | 0 | 39.4 ± 1.4 | 34.4 ± 28 | 0 |
| IL6 | 20604 ± 453 | 27694 ± 3493 | 28744 ± 2008 | 33319 ± 1732 | 27264 ± 10578 | 37971 ± 4381 | 30389 ± 3444 |
| IL8 | 180432 ± 7682 | 183909 ± 10799 | 191568 ± 3311 | 189114 ± 803 | 203349 ± 13125 | 206652 ± 14639 | 227796 ± 12760 |

TABLE 7

Range of concentration determined by ELISA.

| Cytokine | HLSC | MSC |
|---|---|---|
| VEGF | 63-175 (ng/ml) | 153-163 (ng/ml) |
| HGF | 39.5-64 (ng/ml) | 0 |
| IL-6 | 33.6-42.3 (ng/ml) | 26.9-33.8 (ng/ml) |
| IL-8 | 192-221 (ng/ml) | 215-240 (ng/ml) |
| MCP1 | 5491-5869 (pg/ml) | 5032-5962 (pg/ml) |
| MSP1 | 6.4-62.4 (pg/ml) | 0 |

TABLE 8

Range of concentration of selected cytokines determined by multiplex and ELISA

| Cytokine | HLSC | MSC | HLSC | MSC |
|---|---|---|---|---|
| VEGF | 34.9-91 (ng/ml) | 25.9-65.9 (ng/ml) | 63-175 (ng/ml) | 153-163 (ng/ml) |
| HGF | 11.5-20.2 (ng/ml) | 195-485 (pg/ml) | 39.5-64 (ng/ml) | 0 |
| IL-6 | >40 ng/ml | >40 ng/ml | 33.6-42.3 (ng/ml) | 26.9-33.8 (ng/ml) |
| IL-8 | >35 ng/ml | >35 ng/ml | 192-221 (ng/ml) | 215-240 (ng/ml) |
| MCP1 | 1658-8500 (pg/ml) | 600-2296 (pg/ml) | 5491-5869 (pg/ml) | 5032-5962 (pg/ml) |
| MSP1 | ND | ND | 6.4-62.4 (pg/ml) | 0 |

(ND: not determined)

Immunoprecipitation of MSP-1 from HLSC Conditioned Medium and Western Blot

MSP-1 in HLSC culture supernatants was determined by immunoprecipitation and Wester blot. 15 mL of culture supernatant after 24 hour of culture was centrifuged for 70 minutes at 4000×g at 4° C., concentrated on an Amicon 3 KD ultrafilter to 250 μL. For protein precipitation, 1 ml of cold (−20° C.) pure ethanol was added to 250 μl of concentrated supernatant and incubated at −80° C. for overnight. Precipitated proteins were collected after centrifugated at 1,200 g and lysed with 500 □l of RIPA buffer. Immunoprecipitation was carried out for 18 hours using an anti-MSP antibody (R&D system) cross-linked to protein A-Sepharose. For SDS-PAGE, pellets were suspended in 40 μL of 2-beta-mercaptoethanol and heated at 100° C. Proteins were separated by SDS-PAGE in 8% acrylamide gel, transferred to a nitrocellulose membrane. After 1 hour of blocking with 5% non-fat dry milk in Tris-buffered saline containing 0.05% Tween 20, the membrane was incubated overnight with 2 μg/ml of anti-human MSP antibody at 4° C. and, after washed three times, incubated 1 hours at room temperature with goat anti-mouse IgG conjugated with horseradish peroxidise (BioRad). The membrane was revealed with a chemiluminescence reagent and analyzed with chemidoc.

Figure 9:
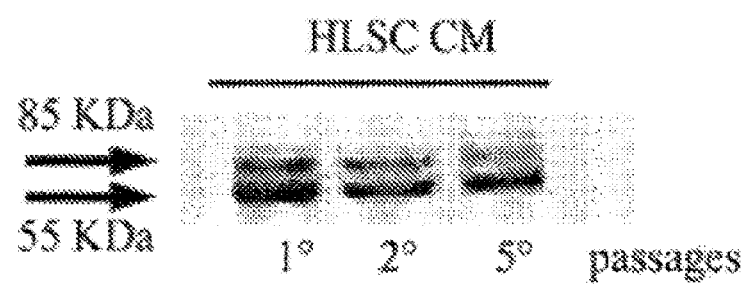
FIG. 9 illustrates the results of SDS-PAGE gel electrophoresis that show immunoprecipitation of MSP from conditioned medium of HLSCs at three different passages (1, 2, 5).

The results are illustrated in FIG. 9, showing immunoprecipitation of MSP from conditioned medium of HLSCs at three different passages (1, 2, 5). The 85-KDa bands represent monomeric MSP (pro-MSP), and the 55-KDa bands the α-chain of dimeric (active) MSP.

Example 5—CM Composition Analysis by Raybio Biotin Label-Based Antibody Array The expression levels of 507 human target proteins derived from HLSC and MSC CM were simultaneously detected. CM were collected after 48 hours culture of 1×10$^6$ cells in the presence of αMEM supplemented with 0.2% of FCS as described in protein array protocol. The panel of molecules included cytokines, chemokines, adipokine, growth factors, angiogenic factors, proteases, soluble receptors, soluble adhesion molecules, and other proteins in cell culture supernatant.

Material and Methods

Preparation of CM. To prepare HLSCs and MSC CM, cells were plated in 100 mm tissue culture dishes at a density of 1×10$^6$ cells per dish. Cells were then culture with complete culture medium for 24-48 hours. After that, medium was replaced with lower serum (0.2% FCS) and then the cells were cultured for 48 hours again once more. The CM were collected, and centrifuged at 1000 g. CM from both cell types were dialyzed before biotin-labeling step. Through a simple process, the primary amine of the proteins in the samples were biotinylated, followed by dialysis to remove free biotin. From here, the newly biotinylated samples were added onto the array membrane and incubated at room temperature. After incubation with HRP-streptavidin, the signals were visualized by chemiluminescence. In this array, an internal control to monitoring the whole process including biotin-label and antibody array was used. Results were analyzed with RayBio Analysis Tool which is a program specifically designed for analysis of RayBio Biotin Label-based Antibody Array. Further details on this assay may be found in the RayBio® Biotin Label-based Human Antibody Array I User Manual.

Figure 10:
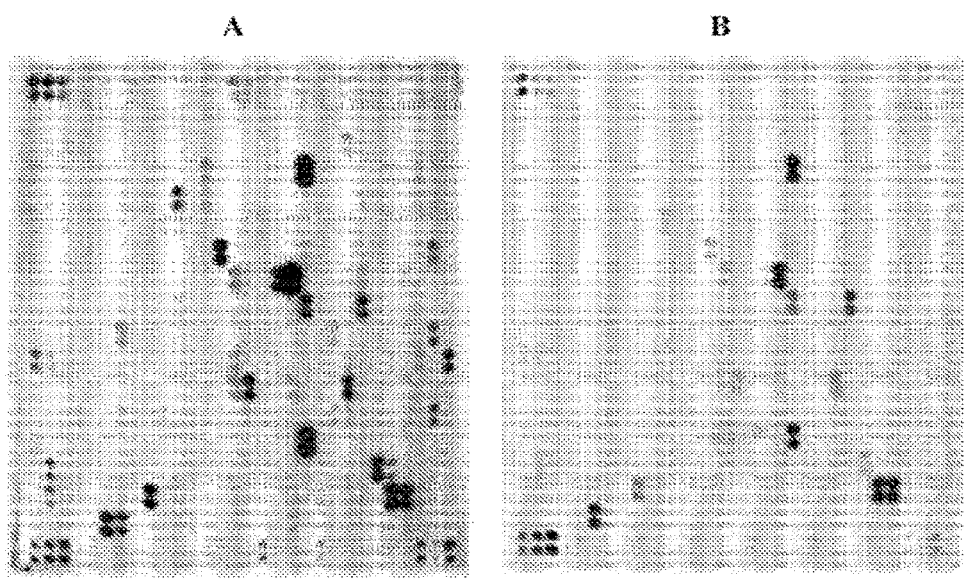
FIG. 10 shows RayBio Biotin Label-based human array maps from HLSCs (A) and MSC-derived supernatant (B).

FIG. 10 shows the RayBio Biotin Label-based human array map from HLSCs (A) and MSC-derived supernatant (B).

The complete results of the RayBio Biotin Label-based Antibody Array assay are summarised below in Table 9.

TABLE 9

| Proteins | HLSC (densitometric analysis | HLSC/MSC ratio |
|---|---|---|
| 6Ckine | 6.11 | 2.06 |
| Activin A | 6.54 | 2.16 |
| Acitvin B | 5.42 | 2.18 |
| Activin C† | 7.27 | 2.56 |
| Activin RIA/ALK-2 | 5.63 | 2.18 |
| Activin RIB/ALK-4 | 5.27 | 1.95 |
| Activin RII A/B | 5.18 | 1.76 |
| Acitvin RIIA | 5.28 | 1.71 |
| Adiponectin/Acrp30 | 5.57 | 1.48 |
| AgRP | 5.67 | 1.59 |
| ALCAM† | 10.30 | 2.62 |
| Angiogenin | 9.40 | 2.38 |
| Angiopoietin-1 | 6.45 | 1.45 |
| Angiopoietin-2 | 5.92 | 1.48 |
| Angiopoietin-4 | 5.62 | 1.40 |
| Angiopoietin-like 1 | 5.76 | 1.36 |
| Angiopoietin-like 2 | 6.51 | 1.51 |

TABLE 9-continued

| Proteins | HLSC (densitometric analysis) | HLSC/MSC ratio |
|---|---|---|
| Angiopoietin-like Factor | 6.26 | 1.53 |
| Angiostatin | 6.90 | 1.66 |
| APJ | 6.00 | 1.40 |
| AR (Amphiregulin) | 6.34 | 1.47 |
| APRIL | 7.03 | 1.47 |
| Artemin | 7.30 | 1.52 |
| Axl | 8.83 | 1.70 |
| B7-1/CD80 | 9.33 | 1.66 |
| BAFF R/TNFRSF13C | 9.12 | 1.48 |
| BCMA/TNFRSF17 | 4.68 | 1.79 |
| BD-1 | 4.64 | 1.77 |
| BDNF | 4.71 | 1.68 |
| beta-Catenin | 4.23 | 1.61 |
| beta-Defensin 2 | 4.31 | 1.63 |
| beta-NGF | 4.38 | 1.66 |
| BIK | 4.56 | 1.73 |
| BLC/BCA-1/CXCL13 | 4.36 | 1.56 |
| BMP-2 | 4.25 | 1.50 |
| BMP-3 | 4.43 | 1.43 |
| BMP-3b/GDF-10 | 4.34 | 1.43 |
| BMP-4 | 4.60 | 1.41 |
| BMP-5 | 4.46 | 1.40 |
| BMP-6 | 4.47 | 1.34 |
| BMP-7 | 4.44 | 1.31 |
| BMP-8 | 4.87 | 1.31 |
| BMP-15 | 4.74 | 1.33 |
| BMPR-IA/ALK-3 | 5.30 | 1.49 |
| BMPR-IB/ALK-6 | 6.35 | 1.69 |
| BMPR-II | 5.76 | 1.59 |
| BTC | 5.71 | 1.61 |
| Cardiotrophin-1/CT-1 | 5.89 | 1.61 |
| CCL14/HCC-1/HCC-3 | 5.92 | 1.50 |
| CCL28/VIC | 6.67 | 1.57 |
| CCR1 | 7.76 | 1.42 |
| CCR2 | 9.00 | 1.63 |
| CCR3 | 8.21 | 1.49 |
| CCR4† | 8.04 | 3.02 |
| CCR5 | 5.02 | 1.97 |
| CCR6 | 5.59 | 2.08 |
| CCR7 | 5.52 | 1.89 |
| CCR8 | 4.43 | 1.51 |
| CCR9 | 4.10 | 1.48 |
| CD14 | 4.21 | 1.55 |
| CD27/TNFRSF7 | 3.94 | 1.50 |
| CD30/TNFRSF8 | 3.70 | 1.38 |
| CD30 Ligand/TNFSF8 | 4.28 | 1.40 |
| CD40/TNFRSF5 | 4.40 | 1.56 |
| CD40 Ligand/TNFSF5/CD154 | 4.14 | 1.38 |
| CD 163 | 3.69 | 1.33 |
| Cerberus 1 | 3.86 | 1.29 |
| Chem R23 | 3.59 | 1.22 |
| Chordin-Like 1 | 3.62 | 1.14 |
| Chordin-Like 2 | 3.74 | 1.16 |
| Csk | 5.97 | 1.51 |
| CLC | 4.23 | 1.20 |
| CNTF | 4.73 | 1.35 |
| CNTF R alpha | 4.51 | 1.29 |
| Coagulation Factor III/Tissue Factor | 4.70 | 1.38 |
| CRIM 1† | 8.98 | 2.55 |
| Cripto-1 | 5.26 | 1.50 |
| CRTH-2 | 5.11 | 1.44 |
| Cryptic | 5.65 | 1.59 |
| CTACK/CCL27 | 6.33 | 1.66 |
| CTGF/CCN2 | 6.97 | 1.77 |
| CTLA-4/CD152 | 10.38 | 2.31 |
| CV-2/Crossveinless-2 | 7.80 | 1.61 |
| CXCL14/BRAK | 6.49 | 2.03 |
| CXCL16 | 4.64 | 1.67 |
| CXCR1/IL-8 RA | 4.56 | 1.61 |
| CXCR2/IL-8 RB | 4.41 | 1.55 |
| CXCR3 | 4.01 | 1.56 |
| CXCR4 (fusin) | 3.85 | 1.44 |
| CXCR5/BLR-1 | 3.84 | 1.41 |
| CXCR6 | 3.92 | 1.40 |
| D6 | 3.77 | 1.38 |
| DAN | 4.02 | 1.36 |
| DANCE | 3.78 | 1.38 |
| DcR3/TNFRSF6B | 3.62 | 1.28 |
| Decorin† | 9.12 | 2.86 |
| Dkk-1 | 4.35 | 1.36 |
| Dkk-3 | 3.41 | 1.12 |
| Dkk-4 | 3.50 | 1.09 |
| DR3/TNFRSF25 | 3.53 | 1.11 |
| DR6/TNFRSF21 | 4.20 | 1.25 |
| DtK | 9.06 | 2.17 |
| EDA-A2† | 237.46 | 2.94 |
| EDAR | 6.79 | 1.88 |
| EDG-1 | 4.43 | 1.25 |
| EGF | 4.63 | 1.30 |
| EGF R/ErbB1 | 4.69 | 1.31 |
| EG-VEGF/PK1 | 5.03 | 1.34 |
| EMAP-II | 6.15 | 1.75 |
| ENA-78 | 6.28 | 1.74 |
| Endocan | 8.34 | 2.14 |
| Endoglin/CD105 | 8.97 | 2.02 |
| Endostatin | 8.59 | 1.53 |
| EN-RAGE | 5.09 | 2.04 |
| Eotaxin/CCL11 | 4.52 | 1.77 |
| Eotaxin-2/MPIF-2 | 4.27 | 1.47 |
| Eotaxin-3/CCL26 | 4.24 | 1.52 |
| Epiregulin | 3.87 | 1.43 |
| ErbB2 | 3.90 | 1.43 |
| ErbB3 | 4.17 | 1.56 |
| ErbB4 | 3.82 | 1.34 |
| Erythropoietin | 4.16 | 1.26 |
| E-Selectin | 3.79 | 1.33 |
| Endothelin† | 14.95 | 3.86 |
| FADD | 3.77 | 1.29 |
| FAM3B | 6.05 | 1.76 |
| Fas/TNFRSF6 | 3.73 | 1.21 |
| Fas Ligand | 3.61 | 1.11 |
| FGF Basic | 3.67 | 1.08 |
| FGF-BP | 3.78 | 1.08 |
| FGF-R3 | 4.05 | 1.19 |
| FGF-R4 | 4.72 | 1.29 |
| FGF-R5† | 17.21 | 2.92 |
| FGF-4 | 4.68 | 1.30 |
| FGF-5 | 4.05 | 1.13 |
| FGF-6 | 4.27 | 1.16 |
| FGF-7/KGF | 4.93 | 1.22 |
| FGF-8 | 4.89 | 1.37 |
| FGF-9 | 5.40 | 1.49 |
| FGF-10/KGF-2 | 5.74 | 1.56 |
| FGF-11 | 6.19 | 1.66 |
| FGF-12 | 8.68 | 1.98 |
| FGF-13 1B | 7.74 | 1.60 |
| FGF-16 | 5.31 | 1.77 |
| FGF-17 | 3.91 | 1.37 |
| FGF-18 | 4.00 | 1.44 |
| FGF-19 | 3.88 | 1.37 |
| FGF-20 | 3.67 | 1.33 |
| FGF-21 | 3.88 | 1.42 |
| FGF-23 | 3.90 | 1.22 |
| FLRG | 3.84 | 1.34 |
| Flt-3 Ligand | 3.69 | 1.32 |
| Follistatin | 5.33 | 1.58 |
| Follistatin-like 1 | 5.81 | 1.15 |
| Fractalkine | 3.94 | 1.28 |
| Frizzled-1 | 3.88 | 1.23 |
| Frizzled-3 | 3.80 | 1.18 |
| Frizzled-4 | 3.78 | 1.21 |
| Frizzled-5 | 4.52 | 1.36 |
| Frizzled-6 | 5.46 | 1.62 |
| Frizzled-7 | 4.17 | 1.23 |
| Galectin-3 | 5.86 | 1.56 |
| GASP-1/WFIKKNRP | 5.03 | 1.44 |
| GASP-2/WFIKKN | 4.39 | 1.20 |
| GCP-2/CXCL6 | 4.69 | 1.26 |
| GCSF | 5.57 | 1.52 |
| G-CSF R/CD 114 | 4.68 | 1.26 |
| GDF1 | 5.00 | 1.28 |
| GDF3 | 6.38 | 1.77 |

TABLE 9-continued

| Proteins | HLSC (densitometric analysis | HLSC/MSC ratio |
|---|---|---|
| GDF5 | 6.55 | 1.74 |
| GDF8 | 6.08 | 1.58 |
| GDF9 | 10.31 | 2.25 |
| GDF11 | 8.84 | 1.70 |
| GDF-15 | 4.64 | 1.34 |
| GDNF | 3.87 | 1.27 |
| GFR alpha-1 | 3.67 | 1.25 |
| GFR alpha-2 | 3.92 | 1.21 |
| GFR alpha-3 | 4.09 | 1.39 |
| GFR alpha-4 | 4.01 | 1.45 |
| GITR/TNFRF18 | 3.80 | 1.33 |
| GITR Ligand/TNFSF18 | 4.04 | 1.44 |
| Glucagon | 3.89 | 1.31 |
| Glut1 | 3.61 | 1.23 |
| Glut2 | 3.73 | 1.22 |
| Glut3 | 3.87 | 1.25 |
| Glut5 | 4.00 | 1.29 |
| Glypican 3† | 34.34 | 2.73 |
| Glypican 5 | 5.27 | 1.48 |
| GM-CSF | 4.20 | 1.24 |
| GM-CSF R alpha | 4.37 | 1.28 |
| Granzyme A | 4.92 | 1.41 |
| GREMLIN | 8.49 | 2.19 |
| GRO† | 21.75 | 3.69 |
| GRO-a | 4.90 | 1.32 |
| Growth Hormone (GH) | 5.17 | 1.34 |
| Growth Hormone R (GHR) | 5.42 | 1.36 |
| HB-EGF | 5.37 | 1.46 |
| HCC-4/CCL16 | 4.91 | 1.33 |
| HCR/CRAM-A/B | 5.09 | 1.39 |
| Hepassocin | 6.08 | 1.61 |
| Heregulin/NDF/GGF/Neuregulin | 6.08 | 1.45 |
| HGF† | 15.29 | 3.38 |
| HGFR | 6.53 | 1.31 |
| HRG-alpha | 4.47 | 1.40 |
| HRG-beta 1 | 4.09 | 1.25 |
| HVEM/TNFRSF14 | 4.06 | 1.24 |
| I-309 | 3.67 | 1.25 |
| ICAM-1 | 3.49 | 1.25 |
| ICAM-2 | 3.28 | 1.16 |
| ICAM-3 (CD50) | 3.77 | 1.15 |
| ICAM-5 | 3.49 | 1.24 |
| IFN-alpha/beta R1 | 3.50 | 1.19 |
| IFN-alpha/beta R2 | 3.52 | 1.18 |
| IFN-beta | 3.66 | 1.19 |
| IFN-gamma | 3.67 | 1.17 |
| IFN-gamma R1 | 3.89 | 1.22 |
| IGFBP-1 | 4.95 | 1.39 |
| IGFBP-2 | 13.69 | 2.11 |
| IGFBP-3 | 6.11 | 1.66 |
| IGFBP-4 | 5.90 | 1.64 |
| IGFBP-6† | 27.78 | 4.59 |
| IGFBP-rp1/IGFBP-7† | 333.01 | 2.75 |
| IGF-I† | 13.74 | 3.15 |
| IGF-I SR | 5.23 | 1.35 |
| IGF-II | 4.76 | 1.26 |
| IGF-II R | 6.57 | 1.69 |
| IL-1 alpha | 9.12 | 2.26 |
| IL-1 beta | 4.87 | 1.30 |
| IL-1 F5/FIL1 delta | 5.25 | 1.42 |
| IL-1 F6/FIL1 epsilon | 7.50 | 1.79 |
| IL-1 F7/FIL1 zeta | 5.73 | 1.37 |
| IL-1 F8/FIL1 eta | 5.91 | 1.25 |
| IL-1 F9/IL-1 H1 | 6.37 | 1.24 |
| IL-1 F10/IL-1HY2 | 4.26 | 1.19 |
| IL-1 R3/IL-1 R AcP | 4.11 | 1.25 |
| IL-1 R4/ST2 | 4.29 | 1.33 |
| IL-1 R6/IL-1 Rrp2 | 3.69 | 1.21 |
| IL-1 R8 | 3.32 | 1.13 |
| IL-1 R9 | 3.32 | 1.07 |
| IL-1 ra | 3.36 | 1.11 |
| IL-1 sRI | 3.29 | 1.09 |
| IL-1 sRII | 3.25 | 1.03 |
| IL-2 | 3.53 | 1.12 |
| IL-2 R alpha | 4.82 | 1.43 |
| IL-2 R beta/CD122 | 3.88 | 1.15 |
| IL-2 R gamma | 4.07 | 1.17 |
| IL-3 | 4.34 | 1.26 |
| IL-3 R alpha | 4.64 | 1.24 |
| IL-4 | 4.72 | 1.25 |
| IL-4 R | 5.53 | 1.11 |
| IL-5 | 6.31 | 1.60 |
| IL-5 R alpha | 16.15 | 2.21 |
| IL-6 | 35.23 | 1.46 |
| IL-6 R | 6.41 | 1.51 |
| IL-7 | 6.01 | 1.51 |
| IL-7 R alpha | 6.10 | 1.30 |
| IL-8 | 38.69 | 1.37 |
| IL-9 | 6.41 | 1.47 |
| IL-10 | 5.27 | 1.39 |
| IL-10 R alpha | 5.42 | 1.36 |
| IL-10 R beta | 5.54 | 1.38 |
| IL-11 | 5.71 | 1.20 |
| IL-12 p40 | 6.30 | 1.17 |
| IL-12 p70 | 4.14 | 1.22 |
| IL-12 R beta 1 | 3.44 | 1.08 |
| IL-12 R beta 2 | 8.52 | 1.70 |
| IL-13 | 3.81 | 1.11 |
| IL-13 R alpha 1 | 4.12 | 1.14 |
| IL-13 R alpha 2 | 3.59 | 1.03 |
| IL-15 | 4.07 | 1.19 |
| IL-15 R alpha | 4.37 | 1.19 |
| IL-16 | 4.16 | 1.17 |
| IL-17 | 4.13 | 1.18 |
| IL-17B | 4.59 | 1.17 |
| IL-17B R | 4.89 | 1.16 |
| IL-17C | 5.24 | 1.23 |
| IL-17D | 5.18 | 1.24 |
| IL-17E | 5.74 | 1.41 |
| IL-17F | 5.96 | 1.40 |
| IL-17R | 5.29 | 1.35 |
| IL-17RC | 9.68 | 2.10 |
| IL-17RD | 6.54 | 1.60 |
| IL-18 BPa | 7.23 | 1.50 |
| IL-18 R alpha/IL-1 R5 | 5.76 | 1.44 |
| IL-18 R beta/AcPL | 5.84 | 1.44 |
| IL-19 | 6.69 | 1.61 |
| IL-20 | 6.79 | 1.58 |
| IL-20 R alpha† | 15.60 | 3.16 |
| IL-20 R beta | 7.48 | 1.34 |
| IL-21 | 3.14 | 0.98 |
| IL-21 R | 3.18 | 0.95 |
| IL-22 | 3.34 | 0.91 |
| IL-22 BP | 3.22 | 0.93 |
| IL-22 R | 3.51 | 0.97 |
| IL-23 | 4.14 | 1.07 |
| IL-23 R | 3.75 | 1.06 |
| IL-24 | 4.14 | 1.07 |
| IL-26 | 4.28 | 1.17 |
| IL-27 | 5.71 | 1.42 |
| IL-28A | 9.23 | 2.20 |
| IL-29 | 5.31 | 1.18 |
| IL-31 | 4.89 | 1.23 |
| IL-31 RA | 5.80 | 1.26 |
| Inhibin A | 5.19 | 1.31 |
| Inhibin B | 5.93 | 1.37 |
| Insulin | 5.29 | 1.25 |
| Insulin R | 5.13 | 1.22 |
| Insulysin/IDE | 7.60 | 1.78 |
| IP-10 | 5.86 | 1.36 |
| I-TAC/CXCL11 | 5.83 | 1.40 |
| Kininostatin/kininogen | 7.18 | 1.75 |
| Kremen-1 | 6.35 | 1.54 |
| Kremen-2† | 13.18 | 3.01 |
| Lck | 7.05 | 1.42 |
| Latent TGF-beta bp1† | 28.04 | 4.90 |
| LBP | 4.34 | 1.23 |
| LECT2 | 3.38 | 1.00 |
| Lefty - A | 3.38 | 1.01 |
| Leptin R | 3.66 | 0.98 |
| Leptin (OB) | 3.52 | 1.03 |
| LFA-1 alpha | 3.75 | 1.05 |

TABLE 9-continued

| Proteins | HLSC (densitometric analysis) | HLSC/MSC ratio |
|---|---|---|
| LIF | 4.12 | 1.09 |
| LIF R alpha | 4.43 | 1.02 |
| LIGHT/TNFSF14 | 4.34 | 1.09 |
| Lipocalin-1 | 4.58 | 1.14 |
| LRP-1 | 9.89 | 1.81 |
| LRP-6 | 29.80 | 2.28 |
| L-Selectin (CD62L) | 5.94 | 1.51 |
| Luciferase | 5.29 | 1.2% |
| Lymphotactin/XCL1 | 8.21 | 1.50 |
| Lymphotoxin beta/TNFSF3 | 5.97 | 1.39 |
| Lymphotoxin beta R/TNFRSF3 | 5.61 | 1.30 |
| MAC-1 | 5.54 | 1.20 |
| MCP-1 | 22.87 | 1.84 |
| MCP-2 | 5.83 | 1.37 |
| MCP-3 | 6.96 | 1.65 |
| MCP-4/CCL13 | 6.09 | 1.48 |
| M-CSF | 6.90 | 1.65 |
| M-CSF R | 7.02 | 1.62 |
| MDC | 8.30 | 1.64 |
| MFG-E8 | 8.93 | 1.62 |
| MFRP | 3.43 | 0.98 |
| MIF | 3.73 | 1.02 |
| MIG | 3.67 | 1.03 |
| MIP-1a | 5.17 | 1.42 |
| MIP-1b | 3.49 | 0.98 |
| MIP-1d | 3.45 | 0.93 |
| MIP 2† | 11.45 | 2.56 |
| MIP-3 alpha | 4.64 | 1.33 |
| MIP-3 beta | 3.68 | 1.03 |
| MMP-1 | 5.06 | 1.20 |
| MMP-2 | 4.30 | 1.14 |
| MMP-3 | 4.08 | 0.75 |
| MMP-7 | 4.49 | 0.93 |
| MMP-8 | 4.80 | 1.15 |
| MMP-9 | 4.25 | 0.98 |
| MMP-10 | 6.05 | 1.44 |
| MMP-11/Stromelysin-3 | 5.23 | 1.22 |
| MMP-12 | 5.12 | 1.33 |
| MMP-13 | 5.75 | 1.40 |
| MMP-14 | 7.60 | 1.79 |
| MMP-15 | 5.71 | 1.39 |
| MMP-16/MT3-MMP | 7.86 | 1.80 |
| MMP-19 | 9.10 | 1.70 |
| MMP-20 | 8.06 | 1.68 |
| MMP-24/MT5-MMP | 6.44 | 1.48 |
| MMP-25/MT6-MMP | 6.20 | 1.36 |
| Musk | 6.62 | 1.41 |
| MSP alpha Chain | 6.85 | 1.40 |
| MSP beta-chain† | 16.76 | 2.65 |
| NAP-2 | 9.61 | 1.71 |
| NCAM-1/CD56 | 5.11 | 1.24 |
| Neuritin | 4.04 | 1.06 |
| NeuroD1 | 3.86 | 1.07 |
| Neuropilin-2 | 3.58 | 1.01 |
| Neurturin | 3.58 | 0.94 |
| NGF R | 3.63 | 1.03 |
| NOV/CCN3 | 3.58 | 1.13 |
| NRG1 Isoform GGF2 | 3.60 | 1.10 |
| NRG1-alpha/HRG1-alpha | 3.58 | 1.03 |
| NRG1-beta1/HRG1-beta1 | 4.12 | 1.20 |
| NRG2 | 4.09 | 1.02 |
| NRG3 | 4.45 | 1.11 |
| NT-3 | 3.73 | 0.96 |
| NT-4 | 4.10 | 0.85 |
| Orexin A | 4.34 | 0.65 |
| Orexin B | 4.60 | 0.55 |
| OSM | 4.89 | 0.69 |
| Osteoactivin/GPNMB | 5.20 | 0.98 |
| Osteocrin | 8.16 | 1.73 |
| Osteoprotegerin/TNFRSF11B† | 265.56 | 5.65 |
| OX40 Ligand/TNFSF4 | 11.27 | 2.49 |
| PARC/CCL18 | 5.35 | 1.26 |
| PD-ECGF | 5.31 | 1.20 |
| PDGF R alpha | 5.73 | 1.32 |
| PDGF R beta | 6.80 | 1.49 |
| PDGF-AA | 7.08 | 1.54 |
| PDGF-AB | 6.91 | 1.52 |
| PDGF-BB | 7.03 | 1.51 |
| PDGF-C | 7.12 | 1.43 |
| PDGF-D | 7.08 | 1.31 |
| PECAM-1/CD31 | 4.21 | 1.18 |
| Pentraxin3/TSG-14 | 11.67 | 2.24 |
| Persephin | 4.49 | 1.20 |
| PF4/CXCL4 | 3.88 | 1.10 |
| PIGF | 3.69 | 1.10 |
| PLUNC | 3.72 | 1.17 |
| Pref-1 | 3.88 | 1.20 |
| Progranulin | 4.96 | 1.52 |
| Prolactin | 4.16 | 1.26 |
| P-selectin | 3.86 | 1.10 |
| RAGE | 3.93 | 1.06 |
| RANK/TNFRSF11A | 4.43 | 1.17 |
| RANTES | 3.86 | 1.05 |
| RELM beta | 3.74 | 0.98 |
| RELT/TNFRSF19L | 4.28 | 0.93 |
| ROBO4 | 4.21 | 1.08 |
| S100 A8/A9 | 4.84 | 1.18 |
| S100A10 | 4.89 | 1.19 |
| SAA | 5.14 | 1.23 |
| SCF | 7.37 | 1.53 |
| SCF R/CD117 | 5.51 | 1.32 |
| SDF-1/CXCL12 | 5.32 | 1.18 |
| sFRP-1 | 6.65 | 1.47 |
| sFRP-3 | 6.42 | 1.35 |
| sFRP-4† | 69.46 | 5.43 |
| sgp130† | 15.48 | 2.93 |
| SIGIRR | 7.82 | 1.55 |
| Siglec-5/CD170 | 7.13 | 1.47 |
| Siglec-9 | 7.91 | 1.63 |
| SLPI | 7.96 | 1.29 |
| Smad 1 | 4.78 | 1.23 |
| Smad 4 | 10.65 | 2.26 |
| Smad 5 | 4.59 | 1.15 |
| Smad 7 | 4.59 | 1.22 |
| Smad 8 | 3.92 | 1.09 |
| SMDF/NRG1Isoform | 4.11 | 1.05 |
| Soggy-1 | 3.92 | 1.14 |
| Sonic Hedgehog (Shh N-terminal) | 3.77 | 1.10 |
| SPARC† | 56.56 | 3.63 |
| Spinesin | 6.40 | 1.68 |
| TACI/TNFRSF13B | 4.40 | 1.10 |
| Tarc | 3.85 | 1.07 |
| TCCR/WSX-1 | 3.80 | 1.00 |
| TECK/CCL25 | 3.79 | 0.98 |
| TFPI | 5.18 | 1.22 |
| TGF-alpha | 4.28 | 1.09 |
| TGF-beta 1 | 4.64 | 1.19 |
| TGF-beta 2 | 4.85 | 1.22 |
| TGF-beta 3 | 5.26 | 1.32 |
| TGF-beta 5 | 5.28 | 1.29 |
| TGF-beta RI/ALK-5 | 6.94 | 1.51 |
| TGF-beta RII | 5.43 | 1.30 |
| TGF-beta RIIb | 5.72 | 1.34 |
| TGF-beta RIII | 6.70 | 1.53 |
| Thrombopoietin (TPO) | 7.40 | 0.94 |
| Thrombospondin (TSP)† | 325.53 | 3.99 |
| Thrombospondin-1† | 281.16 | 3.76 |
| Thrombospondin-2 | 10.81 | 1.94 |
| Thrombospondin-4 | 7.96 | 1.57 |
| Thymopoietin | 7.60 | 1.44 |
| Tie-1 | 4.03 | 0.88 |
| Tie-2 | 3.92 | 0.86 |
| TIMP-1 | 137.73 | 1.08 |
| TIMP-2† | 54.09 | 7.91 |
| TIMP-3 | 7.21 | 1.73 |
| TIMP-4 | 4.31 | 1.05 |
| TL1A/TNFSF15 | 4.70 | 1.14 |
| TLR1 | 4.81 | 1.21 |
| TLR2 | 5.77 | 1.36 |
| TLR3 | 4.47 | 1.06 |
| TLR4 | 4.16 | 1.01 |
| TMEFF1/Tomoregulin-1 | 4.91 | 1.10 |

TABLE 9-continued

| Proteins | HLSC (densitometric analysis) | HLSC/MSC ratio |
|---|---|---|
| TMEFF2 | 4.66 | 1.16 |
| TNF-alpha | 5.07 | 1.26 |
| TNF-beta | 5.36 | 1.26 |
| TNF RI/TNFRSF1A | 8.08 | 1.77 |
| TNF RII/TNFRSF1B | 5.79 | 1.19 |
| TRADD | 5.70 | 1.26 |
| TRAIL/TNFSF10 | 5.83 | 1.26 |
| TRAIL R1/DR4/TNFRSF10A | 6.28 | 1.40 |
| TRAIL R2/DR5/TNFRSF10B | 6.57 | 1.36 |
| TRAIL R3/TNFRSF10C | 6.98 | 1.44 |
| TRAIL R4/TNFRSF10D | 8.02 | 1.38 |
| TRANCE | 9.17 | 1.53 |
| TREM-1 | 4.77 | 0.95 |
| TROY/TNFRSF19 | 5.21 | 1.04 |
| TSG-6 | 5.72 | 1.10 |
| TSLP | 4.90 | 1.03 |
| TWEAK/TNFSF12 | 5.00 | 1.03 |
| TWEAK R/TNFRSF12 | 5.14 | 1.07 |
| Ubiquitin + 1 | 4.92 | 1.03 |
| uPA | 4.94 | 0.90 |
| uPAR | 5.41 | 1.11 |
| Vasorin | 6.12 | 1.27 |
| VCAM-1 (CD106) | 5.02 | 1.11 |
| VE-Cadherin | 5.20 | 1.18 |
| VEGF | 10.00 | 1.61 |
| VEGF R2 (KDR) | 5.73 | 1.25 |
| VEGF R3 | 5.48 | 1.19 |
| VEGF-B | 5.24 | 1.15 |
| VEGF-C | 7.98 | 1.60 |
| VEGF-D | 6.11 | 1.18 |
| VEGI/TNFSF15 | 6.03 | 1.20 |
| WIF-1 | 6.07 | 1.21 |
| WISP-1/CCN4 | 6.68 | 1.30 |
| XEDAR | 7.81 | 1.46 |

Based on a HLSC/MSC ratio equal or over 2.5, a total of 25 proteins were identified as those which are most likely to provide a contribution to the CM's activity. Such proteins are highlighted in Table 9.

Example 6—Comparison of the Effects of HLSCs- and HLSCs-CM-Treatments on the In Vivo FHF Model D-galactosamine/Endotoxin In Vivo Model of Acute Toxic Lethal Hepatitis The mechanisms underlying the hepatotoxic action of galactosamine occurs due to a high accumulation of UDP-galactosamine derivatives in the liver, leading to a depletion of hepatic UTP. As a result biosynthesis of macromolecules (RNA, proteins, glycoproteins, glycogen, etc.) ceases. These alterations lead to eventual cell damage and cell death, which at later stages of the reaction may be identified by the increase of liver enzymes in the blood and by histology. At the same time, endotoxin induced the production of tumor necrosis factor a (TNF-a)—that developed a massive hepatocyte apoptosis. We developed this in vivo model in SCID mice for studied the action of HLSC in this lethal in vivo system.

Methods

Animals and Experimental Protocols.

Six- to 7-week-old male SCID mice were housed in animal facilities with free access to food and water. These animals were given an intraperitoneal injection of 500 μL saline containing 0.125 μg LPS and 18 mg GaIN. The mice were injected intraperitoneally with $30 \times 10^6$ of HLSC after 2 hours of D-GaIN/LPS injection.

A second group of SCID mice were inoculated intraperitoneally with 1 ml of supernatant of HLSC in saline at the same time, 30 minutes and 2 hours after the injection of LPS and GaIN. Control mice were given an injection of a mixture of LPS and GaIN.

Production of Supernatant from HLSC in the T-Flask:

For the generation of CM from HLSC (CM-HLSC), cells were allowed to grow to 60% to 70% confluence (approximately $2 \times 10^6$ HLSC per 75-cm$^2$ flask), washed thoroughly, and cultured in 10 mL serum-free alpha-MEM medium supplemented with 0.05% human serum albumin (GMP produced). Conditioned medium was collected 24 hours later and concentrated 25-fold using ultrafiltration units (Millipore, Bedford, Mass.) with a 3-kDa cut-off.

Histological Analysis:

Necrosis of liver were analyzed through H&E staining, proliferation (PCNA staining) and TUNEL (apoptotic cells).

Western Blot:

Western Blot was performed for detection of BAX and BclXS/L. Livers were homogenized and lysed at 4° C. for 1 hour in lysis buffer (50 mmol/L Tris-HCl, pH 8.3, 1% Triton X-100, 10 μmol/L phenylmethyl sulfonyl fluoride, 10 μmol/L leupeptin, and 100 U/ml aprotinin) and centrifuged at 15,000 g. The protein contents of the CM were measured by the Bradford method. Aliquots containing 200 μg of protein of livers lysates were subjected to 10% sodium dodecyl sulfate-polyacrylamide gel electrophoresis under reducing conditions and electro blotted onto nitrocellulose membrane filters. The blots were blocked with 5% nonfat milk in 20 mmol/L Tris-HCl, pH 7.5, 500 mmol/L NaCl plus 0.1% Tween (TBS-T). The membranes were subsequently immunoblotted overnight at 4° C. with the relevant primary antibodies at the appropriate concentration. After extensive washings with TBS-T, the blots were incubated for 1 hour at room temperature with peroxidase-conjugated isotype-specific secondary antibodies, washed with TBS-T, developed with ECL detection reagents for 1 minute, and exposed to X-Omat film. The following antibodies were used: anti-BAX monoclonal antibody and anti-BclXS/L polyclonal antibody from Santa Cruz Biotechnology.

Results

To assess possible beneficial effects HLSC on the lethality of mice given endotoxin (LPS) and GaIN, survival studies were performed using 6 mice. The % of animal survival injected with 0.125 μg LPS and 18 mg GaIN and $30 \times 10^6$ HLSC was 75%. The % of animal survival injected with concentrated 1 ml of supernatant of HLSC in saline at the same time, 30 minutes and 2 hours after the injection of LPS and 18 mg GaIN was 70% (n=17). Levels of Serum alanine transaminase (ALT) decreased from 273 U/L to 57 U/L and serum aspartate transaminase (AST) decreased from 1693 U/L to 291 U/L both after 7 days of injection of HLSC. Levels of AST decreased from 1693 U/L to 1000 U/L both after 6 days of injection of CM-HLSC.

The Histological analysis of liver sections after 7 days of injection of HLSC showed a decreased index of apoptosis and necrosis.

The Histological analysis of liver sections after 3, and 6 days of supernatant treatment showed a decreased index of apoptosis (TUNEL) and necrosis. A massive tissue regeneration was observed. These finding correlated with an increases of tissue proliferation index (PCNA staining). By western blot it was shown that there was an upregulation of the pro-apoptotic protein BAX in animal treated with GalN/LPS along and a downregulation at the different time point in both concentrated supernatant. In the case of the expression of the pro-apoptotic protein BcLX/L it was observed an upregulation of this protein in animal treated with the concentrated supernatant and a downregulation of the expression in animal treated with GalN/LPS alone.

The results mentioned above are illustrated in FIGS. 11-13.

Figure 11A:
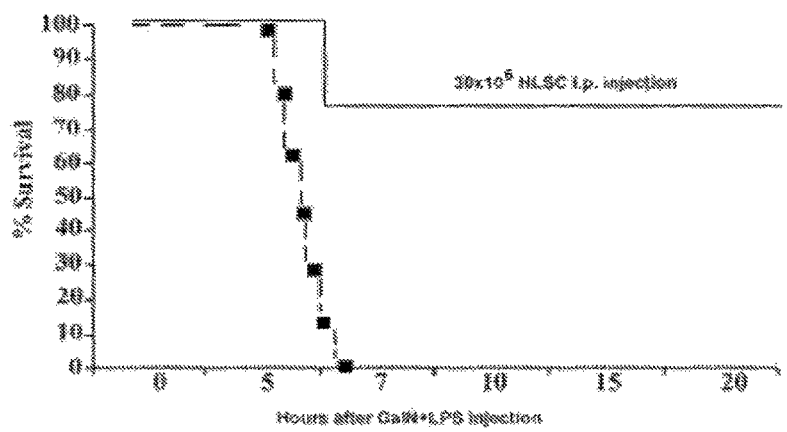
FIG. 11a graphically depicts test results showing mice survival rate (%) over time in an LPS/GaIN lethal model injected with HLSC.

FIG. 11a shows mice survival in LPS/GalN lethal model injected with HLSC (n=6).

Figure 11B:
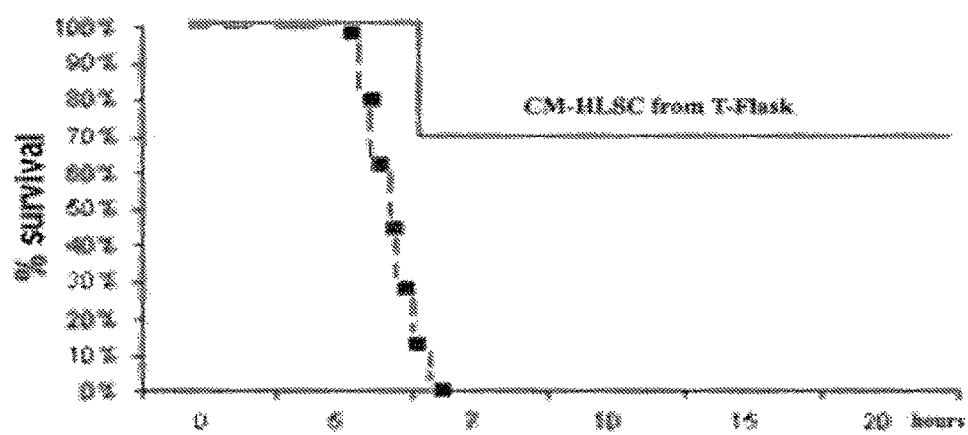
FIG. 11b graphically depicts test results showing mice survival rate (%) over time in an LPS/GaIN lethal model injected with concentrated HLSC.

FIG. 11b shows mice survival in LPS/GalN lethal model injected with HLSC concentrated (n=17).

Figure 12:
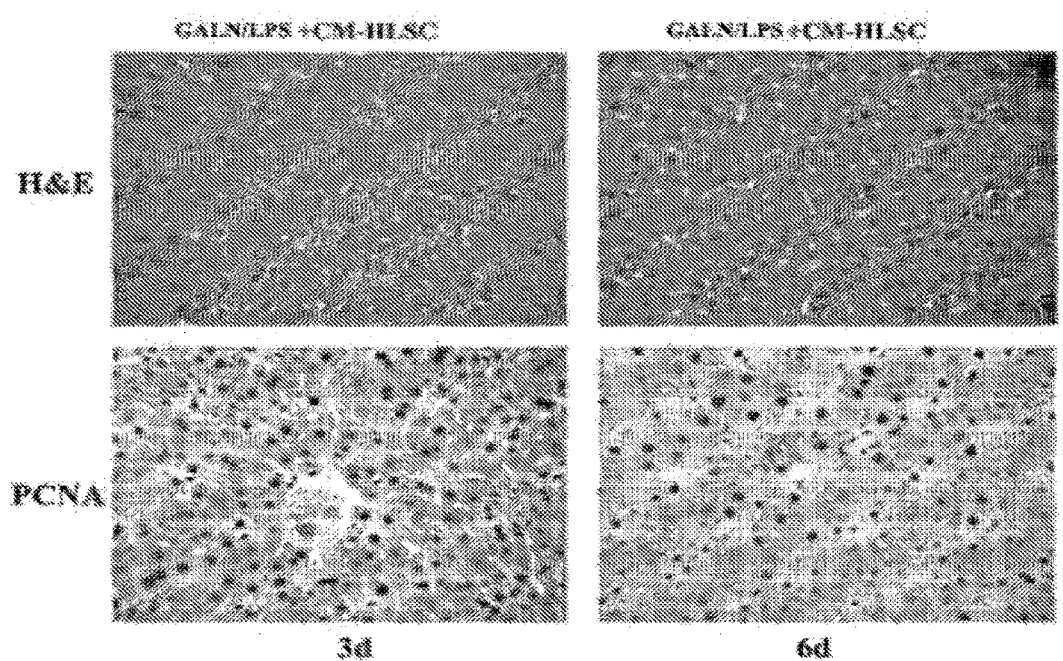
FIG. 12 shows the H&E and PCNA staining of GaIN/LPS treated SCID mice injected with concentrated CM.

FIG. 12 shows the H&E and PCNA staining of GalN/LPS treated SCID mice injected with concentrated CM from HLSC purified from T-Flask after 3 and 6 days of liver failure induction (GalN/LPS).

Figure 13:
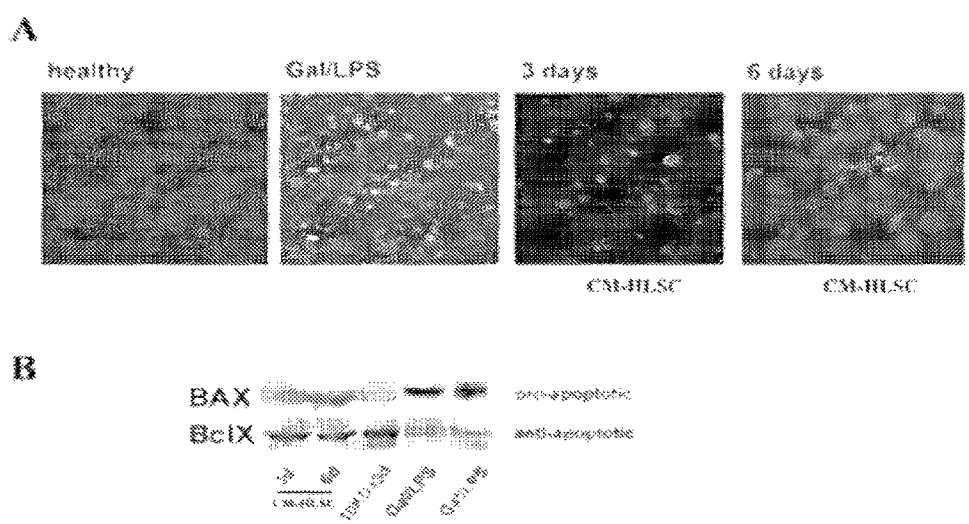
FIG. 13 shows the results of the TUNEL assay to evaluate apoptotic hepatocytes.

FIG. 13 shows the results of the TUNEL assay to evaluate apoptotic hepatocytes. The presence of the pro-apoptotic protein BAX and the anti-apoptotic protein BclX was evaluated by Western blot analysis.

The invention claimed is:

1. A conditioned medium obtained by culturing a non-oval human liver pluripotent progenitor cell line, characterized in that it is free of cells.

2. A pharmaceutical comprising a pharmaceutically effective amount of the conditioned medium according to claim 1 and a pharmaceutically acceptable carrier or diluent.

3. A method of treating an organ injury or failure comprising administering to a subject in need thereof a therapeutically effective amount of a pharmaceutical composition according to claim 2.

* * * * *